US011179512B2

(12) United States Patent
Locke et al.

(10) Patent No.: US 11,179,512 B2
(45) Date of Patent: Nov. 23, 2021

(54) MULTI-LAYER WOUND FILLER FOR EXTENDED WEAR TIME

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 570 days.

(21) Appl. No.: 16/000,215

(22) Filed: Jun. 5, 2018

(65) Prior Publication Data

US 2018/0353663 A1  Dec. 13, 2018

Related U.S. Application Data

(60) Provisional application No. 62/592,950, filed on Nov. 30, 2017, provisional application No. 62/576,498, (Continued)

(51) Int. Cl.
*A61M 1/00* (2006.01)
*A61F 13/02* (2006.01)
*A61F 13/00* (2006.01)

(52) U.S. Cl.
CPC .......... *A61M 1/90* (2021.05); *A61F 13/00063* (2013.01); *A61F 13/00068* (2013.01);
(Continued)

(58) Field of Classification Search
CPC .............. A61M 1/0088; A61M 1/0058; A61M 1/0084; A61M 2205/3331;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU    550575 B2    3/1986
AU    745271 B2    3/2002
(Continued)

OTHER PUBLICATIONS

Definition of "bonded," Merriam-Webster, www.https://www.merriam-webster.com/dictionary/bonded, retrieved Dec. 11, 2020.
(Continued)

*Primary Examiner* — Tatyana Zalukaeva
*Assistant Examiner* — Jessica R Arble

(57) ABSTRACT

A dressing or wound filler comprising a laminate structure of film materials. In one example embodiment, a dressing may include a first layer comprising a first film, a second layer adjacent to the first layer and comprising a second film, and a third layer comprising a material having closed cells. The first layer may further include a plurality of fluid restrictions. The second layer may include blisters and apertures to allow fluid transfer through the second film. The third layer may include closed cells and apertures between the closed cells to allow fluid transfer through the third layer. The dressing may further include a fourth layer adjacent to the third layer opposite the second layer, which may include a fourth film having blisters and apertures. The dressing may also include a fifth layer, which may be adjacent to the fourth layer opposite the third layer. The fifth layer may include a film and a second plurality of fluid restrictions.

17 Claims, 12 Drawing Sheets

Related U.S. Application Data filed on Oct. 24, 2017, provisional application No. 62/565,754, filed on Sep. 29, 2017, provisional application No. 62/516,540, filed on Jun. 7, 2017, provisional application No. 62/516,550, filed on Jun. 7, 2017, provisional application No. 62/516,566, filed on Jun. 7, 2017.

(52) U.S. Cl.
CPC ...... *A61F 13/0206* (2013.01); *A61F 13/0216* (2013.01); *A61M 1/0058* (2013.01); *A61M 1/85* (2021.05); *A61F 2013/00319* (2013.01); *A61F 2013/00357* (2013.01); *A61M 2205/0216* (2013.01); *A61M 2205/3317* (2013.01); *A61M 2205/3331* (2013.01); *A61M 2205/3337* (2013.01); *A61M 2205/3344* (2013.01); *A61M 2210/1021* (2013.01)

(58) Field of Classification Search
CPC .. A61M 2205/3317; A61M 2205/3344; A61M 2205/0216; A61M 2205/3337; A61M 2210/1021; A61F 13/00068; A61F 13/0206; A61F 13/0216; A61F 13/00063; A61F 2013/00357; A61F 2013/00319
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,654,060 A | 4/1972 | Goldman |
| 3,682,180 A | 8/1972 | McFarlane |
| 3,826,254 A | 7/1974 | Mellor |
| 3,930,096 A | 12/1975 | Gilpatrick |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,173,046 A | 11/1979 | Gallagher |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,541,426 A | 9/1985 | Webster |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,313 A | 5/1994 | Karami et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,352 A | 9/1995 | Nishino et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A | 6/1997 | Fabo |
| 5,636,643 A | 6/1997 | Argenta et al. |
| 5,645,081 A | 7/1997 | Argenta et al. |
| 5,720,714 A * | 2/1998 | Penrose ............... A61F 13/023 602/6 |
| 5,842,503 A | 12/1998 | Foley |
| 5,951,505 A | 9/1999 | Gilman et al. |
| 5,981,822 A | 11/1999 | Addison |
| 6,019,511 A | 2/2000 | Thomas et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,468,626 B1 | 10/2002 | Takai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 * | 12/2010 | Weston ............... A61M 1/0027 604/313 |
| 7,867,206 B2 | 1/2011 | Lockwood et al. |

(56) References Cited

U.S. PATENT DOCUMENTS

| | | |
|---|---|---|
| 7,880,050 B2 | 2/2011 | Robinson et al. |
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blatt et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2001/0043943 A1 | 11/2001 | Coffey |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0203011 A1 | 10/2003 | Abuelyaman et al. |
| 2004/0030304 A1 | 2/2004 | Hunt et al. |
| 2004/0126413 A1 | 7/2004 | Sigurjonsson et al. |
| 2004/0138604 A1 | 7/2004 | Sigurjonsson et al. |
| 2004/0148756 A1 | 8/2004 | Pommer |
| 2004/0261295 A1 | 12/2004 | Meschter |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2008/0300555 A1* | 12/2008 | Olson ............... A61F 13/00068 604/313 |
| 2009/0047495 A1 | 2/2009 | Hubbs |
| 2009/0082746 A1 | 3/2009 | Thomas et al. |
| 2009/0221979 A1 | 9/2009 | Huang et al. |
| 2009/0234307 A1 | 9/2009 | Vitaris |
| 2009/0293887 A1 | 12/2009 | Wilkes et al. |
| 2010/0030178 A1 | 2/2010 | MacMeccan et al. |
| 2010/0036334 A1 | 2/2010 | Heagle et al. |
| 2010/0063484 A1 | 3/2010 | Heagle |
| 2010/0069863 A1 | 3/2010 | Olson |
| 2010/0106115 A1 | 4/2010 | Hardman et al. |
| 2010/0159192 A1 | 6/2010 | Cotton |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0117178 A1 | 5/2011 | Junginger |
| 2011/0160686 A1 | 6/2011 | Ueda et al. |
| 2011/0213287 A1 | 9/2011 | Lattimore et al. |
| 2011/0213319 A1* | 9/2011 | Blott ................ A61F 13/00063 604/291 |
| 2011/0224631 A1* | 9/2011 | Simmons .......... A61F 13/00995 604/319 |
| 2011/0282309 A1 | 11/2011 | Adie et al. |
| 2011/0313374 A1 | 12/2011 | Lockwood et al. |
| 2012/0046603 A1* | 2/2012 | Vinton ............. A61F 13/00051 604/24 |
| 2012/0157945 A1 | 6/2012 | Robinson et al. |
| 2012/0209226 A1 | 8/2012 | Simmons et al. |
| 2012/0238932 A1 | 9/2012 | Atteia et al. |
| 2013/0053748 A1 | 2/2013 | Cotton |
| 2013/0152945 A1 | 6/2013 | Locke et al. |
| 2013/0261534 A1 | 10/2013 | Niezgoda et al. |
| 2014/0031771 A1 | 1/2014 | Locke et al. |
| 2014/0052041 A1 | 2/2014 | Barberio |
| 2014/0094730 A1 | 4/2014 | Greener et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1 | 8/2014 | Von Wolff et al. |
| 2014/0350494 A1 | 11/2014 | Hartwell et al. |
| 2014/0364819 A1 | 12/2014 | VanDelden |
| 2015/0038933 A1 | 2/2015 | Day et al. |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0141941 A1 | 5/2015 | Allen et al. |
| 2015/0174291 A1 | 6/2015 | Zimnitsky et al. |
| 2015/0174304 A1 | 6/2015 | Askem et al. |
| 2015/0290042 A1 | 10/2015 | Freer et al. |
| 2015/0290050 A1 | 10/2015 | Wada |
| 2015/0320434 A1* | 11/2015 | Ingram .............. A61M 1/0088 606/131 |
| 2015/0320602 A1 | 11/2015 | Locke et al. |
| 2015/0320603 A1 | 11/2015 | Locke et al. |
| 2016/0000610 A1 | 1/2016 | Riesinger |
| 2016/0015571 A1 | 1/2016 | Robinson et al. |
| 2016/0022885 A1 | 1/2016 | Dunn et al. |
| 2016/0030646 A1* | 2/2016 | Hartwell ........... A61F 13/00068 604/319 |
| 2016/0144084 A1 | 5/2016 | Collinson et al. |
| 2016/0144085 A1* | 5/2016 | Melin ............... A61F 13/00068 604/319 |
| 2016/0166744 A1 | 6/2016 | Hartwell |
| 2016/0199546 A1 | 7/2016 | Chao |
| 2016/0199550 A1 | 7/2016 | Seddon et al. |
| 2016/0220742 A1 | 8/2016 | Robinson et al. |
| 2016/0262672 A1 | 9/2016 | Hammond et al. |
| 2016/0354253 A1 | 12/2016 | Hunt et al. |
| 2017/0014273 A1 | 1/2017 | Woodroof |
| 2017/0079846 A1 | 3/2017 | Locke et al. |
| 2017/0095374 A1 | 4/2017 | Lauer |
| 2017/0172807 A1 | 6/2017 | Robinson et al. |
| 2017/0209312 A1 | 7/2017 | Kanchagar et al. |
| 2017/0258640 A1 | 9/2017 | Ahsani Ghahreman et al. |
| 2017/0312406 A1 | 11/2017 | Svensby |
| 2017/0348154 A1 | 12/2017 | Robinson et al. |
| 2018/0071148 A1 | 3/2018 | Lockwood et al. |
| 2018/0289872 A1 | 10/2018 | Coulthard et al. |
| 2018/0296394 A1* | 10/2018 | Barberio ................ A61F 5/058 |
| 2019/0184075 A1* | 6/2019 | Roos ................ A61F 13/00068 |

FOREIGN PATENT DOCUMENTS

| | | |
|---|---|---|
| AU | 755496 B2 | 12/2002 |
| CA | 2005436 A1 | 6/1990 |
| CN | 106390213 A | 2/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0174803 A2 | 3/1986 |
| EP | 0358302 A2 | 3/1990 |

(56) References Cited

FOREIGN PATENT DOCUMENTS

| | | | |
|---|---|---|---|
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2468905 A | 9/2010 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 9319709 A1 | 10/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 0185248 A1 | 11/2001 | |
| WO | 2007113597 A2 | 10/2007 | |
| WO | 2010061228 A1 | 6/2010 | |
| WO | 2011008497 A2 | 1/2011 | |
| WO | WO-2011121127 A1 * | 10/2011 | ....... A61F 13/00068 |
| WO | 2011135286 A1 | 11/2011 | |
| WO | 2014140608 A1 | 9/2014 | |
| WO | 2015098373 A1 | 7/2015 | |
| WO | 2015168681 A1 | 11/2015 | |
| WO | 2015173547 A1 | 11/2015 | |
| WO | 2015193257 A1 | 12/2015 | |
| WO | 2016014645 A1 | 1/2016 | |
| WO | 2016015001 A2 | 1/2016 | |
| WO | 2017040045 A1 | 3/2017 | |
| WO | 2017119996 A1 | 7/2017 | |

OTHER PUBLICATIONS

Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001, pp. 6646-6652.
Office Action for related U.S. Appl. No. 16/000,368, dated Dec. 14, 2020.
Office Action for related U.S. Appl. No. 16/000,284, dated Jun. 8, 2020.
Office Action for related U.S. Appl. No. 15/997,833, dated Jun. 19, 2020.
Office Action for related U.S. Appl. No. 15/997,809, dated Aug. 5, 2020.
Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Office Action for related U.S. Appl. No. 15/997,818, dated Jan. 27, 2021.
Office Action for related U.S. Appl. No. 15/997,841, dated Jan. 27, 2021.
Office Action for related U.S. Appl. No. 15/997,809, dated Jan. 28, 2021.
Louis C. Argenta, MD and Michael J. Morykwas, PhD; Vacuum-Assisted Closure: A New Method for Wound control and Treatment: Clinical Experience; Annals of Plastic Surgery; vol. 38, No. 6, Jun. 1997; pp. 563-576.
Susan Mendez-Eatmen, RN; "When wounds Won't Hear" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

(56) References Cited

OTHER PUBLICATIONS

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyethylene-Single-Sided-Medical-Tape-63-Liner/?N=5002385+8729793+3294739632&rt=rud; accessed May 21, 2019>.
3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Sided-Thermoplastic-Elastomer-TPE-Medical-Incise-Tape/?N=5002385+4294834151&rt=d; accessed May 21, 2019>.
International Search Report and Written Opinion for related application PCT/US2018/036013, dated Aug. 7, 2018.
International Search Report and Written Opinion for related application PCT/US2018/035945, dated Aug. 24, 2018.
International Search Report and Written Opinion for related application PCT/US2018/036074, dated Aug. 24, 2018.
International Search Report and Written Opinion for related application PCT/US2018/035957, dated Sep. 28, 2018.
International Search Report and Written Opinion for related application PCT/US2018/035995, dated Oct. 1, 2018.
International Search Report and Written Opinion for related application PCT/US2018/036021, dated Aug. 24, 2018.
International Search Report and Written Opinion for related application PCT/US2018/036019, dated Oct. 18, 2018.
International Search Report and Written Opinion for related application PCT/US2018/036054, dated Aug. 24, 2018.
International Search Report and Written Opinion for related application PCT/US2018/036049, dated Aug. 29, 2018.
International Search Report and Written Opinion for related application PCT/US2018/036077, dated Aug. 24, 2018.
International Search Report and Written Opinion for related application PCT/US2018/036129, dated Oct. 8, 2018.
Heit, et al., "Foam Pore Size Is a Critical Interface Parameter of Suction-Based Wound Healing Devices," copyright 2012 by the American Society of Plastic Surgeons (www. PRSJournal.com) (Year: 2011).
Office Action for related U.S. Appl. No. 16/000,284, dated Sep. 23, 2019.
Office Action for related U.S. Appl. No. 15/997,833, dated Mar. 26, 2021.
Chinese Office Action for related application 2018800367248, dated Apr. 28, 2021.
Office Action for related U.S. Appl. No. 15/997,833, dated Jun. 7, 2021.
Office Action for related U.S. Appl. No. 15/997,841, dated Jun. 8, 2021.
Chinese Office Action for related application 201880048393X, dated May 26, 2021.
Office Action for related U.S. Appl No. 15/997,809, dated Jul. 8, 2021.
Chinese Office Action for related application 2018800436430, dated Jun. 8, 2021.
Office Action for related U.S. Appl. No. 15/997,923, dated Jul. 23, 2021.
Office Action for related U.S. Appl. No. 15/997,818, dated Aug. 10, 2021.
Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.

* cited by examiner

MULTI-LAYER WOUND FILLER FOR EXTENDED WEAR TIME

RELATED APPLICATION

This application claims the benefit, under 35 U.S.C. § 119(e), of the filing of U.S. Provisional Patent Application Ser. No. 62/592,950, entitled "MULTI-LAYER WOUND FILLER FOR EXTENDED WEAR TIME," filed Nov. 30, 2017; U.S. Provisional Patent Application Ser. No. 62/576,498, entitled "SYSTEMS, APPARATUSES, AND METHODS FOR NEGATIVE-PRESSURE TREATMENT WITH REDUCED TISSUE IN-GROWTH," filed Oct. 24, 2017; U.S. Provisional Patent Application Ser. No. 62/565,754, entitled "COMPOSITE DRESSINGS FOR IMPROVED GRANULATION AND REDUCED MACERATION WITH NEGATIVE-PRESSURE TREATMENT," filed Sep. 29, 2017; U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017, each of which is incorporated herein by reference for all purposes.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing or wound filler may comprise a laminate structure of film materials. Outer layers may comprise perforated or fenestrated film configured to face a tissue site. Examples of material suitable for outer layers include polythene, polyurethane, and ethyl methyl acrylate (EMA). The outer layers may have linear perforations or fenestrations formed over the surface. The size and spacing of the perforations or fenestrations may vary. In some examples, the length of the perforations or fenestrations may be between 2 millimeters and 4 millimeters, spaced between 2 millimeters and 4 millimeters apart along their length and from side to side. The width of perforations may be between 0.4 millimeters and 1 millimeter in some examples. Suitable perforations may be formed, for example, by laser, ultrasonics, or other heat means. Intermediate spacing layers between the outer layers can manifold fluid, provide a compressible filler that can conform to spaces and curves, and can present a barrier to tissue in-growth. The outer layers may be more hydrophobic than the intermediate layers in some examples.

More generally, in some embodiments, a dressing may include a first layer comprising a first film of non-porous material, a second layer adjacent to the first layer and comprising a second film of non-porous material, and a third layer comprising a non-porous material having closed cells. The first layer may further include a plurality of fluid restrictions. The second film of non-porous material of the second layer may include blisters and first apertures to allow fluid transfer through the second film. The non-porous material of the third layer may include closed cells and second apertures between the closed cells to allow fluid transfer through the third layer. The dressing may additionally include a fourth layer adjacent to the third layer opposite the second layer and a fifth layer adjacent to the fourth layer opposite the third layer. The fourth layer may include a third film of non-porous material having blisters and fourth apertures for allowing fluid transfer through the fourth layer. The fifth layer may include a fourth film of non-porous material and a second plurality of fluid restrictions.

In other example embodiments, a wound filler for use with negative-pressure treatment may include a manifold layer comprising a first layer, a second layer, and a third layer, where the second layer and the third layer are laminated to the manifold layer. The first layer of the manifold layer may include closed cells and apertures configured to manifold fluid through the manifold layer. The second layer and the third layer may each include a film of a hydrophobic material and perforations or fenestrations configured to transfer fluid through the film. In some embodiments, the manifold layer may further include a fourth layer having blisters and apertures configured to manifold fluid through the manifold layer.

In still further example embodiments, a system for treating a tissue site may include a wound filler having a first layer, second layer, and third layer, and the system may additionally include a fourth layer and an interface. The first layer of the wound filler may comprise a first film of non-porous material and a plurality of fluid restrictions. The second layer may be adjacent to the first layer and may comprise a second film of non-porous material having blisters and first apertures. The third layer may comprise a non-porous material having closed cells and second apertures between the closed cells. The fourth layer may be coupled to the first layer opposite the second layer and may comprise a polymer drape. The interface may be adapted to be coupled to the fourth layer. The system may further include a negative-pressure source adapted to be fluidly connected to the wound filler through the interface.

In yet further example embodiments, a wound filler may include a first layer, a second layer, a third layer, a fourth layer, a fifth layer, and a sixth layer. The first layer may comprise a first film of non-porous material and a first plurality of fluid restrictions. The second layer may be adjacent to the first layer and may comprise a second film of non-porous material having blisters and first apertures. The third layer may comprise a first plurality of closed cells and second apertures between the closed cells. The fourth layer may comprise a second plurality of closed cells and third apertures between the closed cells. The fifth layer may be adjacent to the fourth layer opposite the third layer and may comprise a third film of non-porous material having blisters and fourth apertures. The sixth layer may be adjacent the fifth layer and may comprise a fourth film of non-porous material and a second plurality of fluid restrictions. Additionally, the wound filler may include a seventh layer positioned between the third layer and the fourth layer, which may comprise a third plurality of closed cells.

In other example embodiments, a dressing may include a first layer comprising a first film of non-porous material and a second layer adjacent to the first layer, the second layer comprising a second film of non-porous material. The first layer may comprise a first plurality of fluid restrictions. The second layer may comprise blisters and first apertures to allow fluid transfer through the second film.

In yet another example embodiment, a manifold for use with negative-pressure treatment may include a first film of non-porous material, a second film of non-porous material, and a plurality of closed cells formed between the first film and the second film. The first film may include a plurality of fluid restrictions. The second film may comprise first apertures.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
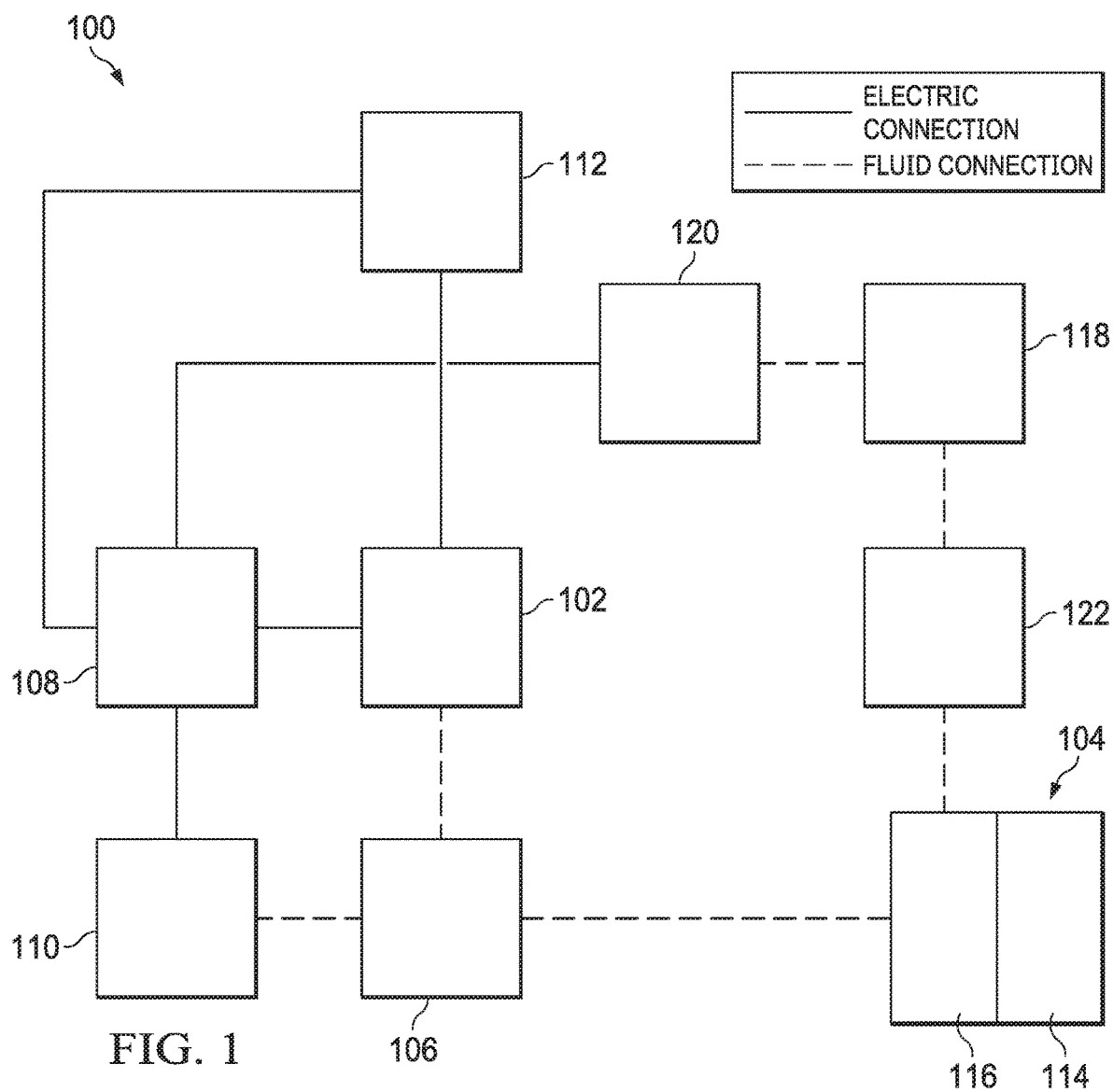
FIG. 1 is a functional block diagram of an example embodiment of a therapy system that can provide tissue treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of one or more dressing layers, such as a tissue interface 114, a cover 116, or both in some embodiments.

The therapy system 100 may also include a source of instillation solution, such as saline, for example. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution to a tissue site. For example, the instillation regulator 122 may comprise a piston that can be pneumatically actuated by the negative-pressure source 102 to draw instillation solution from the solution source 118 during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108 and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108. The negative-pressure source may be fluidly coupled to one or more distribution components, which provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components, including sensors and data communication devices. In some embodiments, for example, a dressing interface may facilitate coupling a fluid conductor to the dressing 104. For example, such a dressing interface may be a SENSA-T.R.A.C.™ Pad available from KCI of San Antonio, Tex.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−9.9 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezo-resistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. If the tissue site is a wound, for example, the tissue interface 114 may partially or completely fill the wound, or may be placed over the wound. The tissue interface 114 may take many forms and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. The tissue interface 114 may take many forms and have more than one layer in some embodiments. Moreover, one or more surfaces of the tissue interface 114 may have projections or an uneven, coarse, or jagged profile that can induce strains and stresses on a tissue site, which can promote granulation at the tissue site.

Additionally, the tissue interface 114 may comprise, consist, or function as a manifold. In this context, a "manifold" generally includes any substance or structure providing a plurality of pathways adapted to collect or distribute fluid, which may involve moving fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source of negative pressure. Furthermore, in some embodiments, the fluid path may be reversed or a secondary fluid path may be provided to facilitate delivering fluid across a tissue site. In some embodiments, a manifold may additionally or alternatively comprise projections that form interconnected fluid pathways. For example, a manifold may be molded to provide surface projections that define interconnected fluid pathways.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide may provide effective breathability and mechanical properties. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy are generally well known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
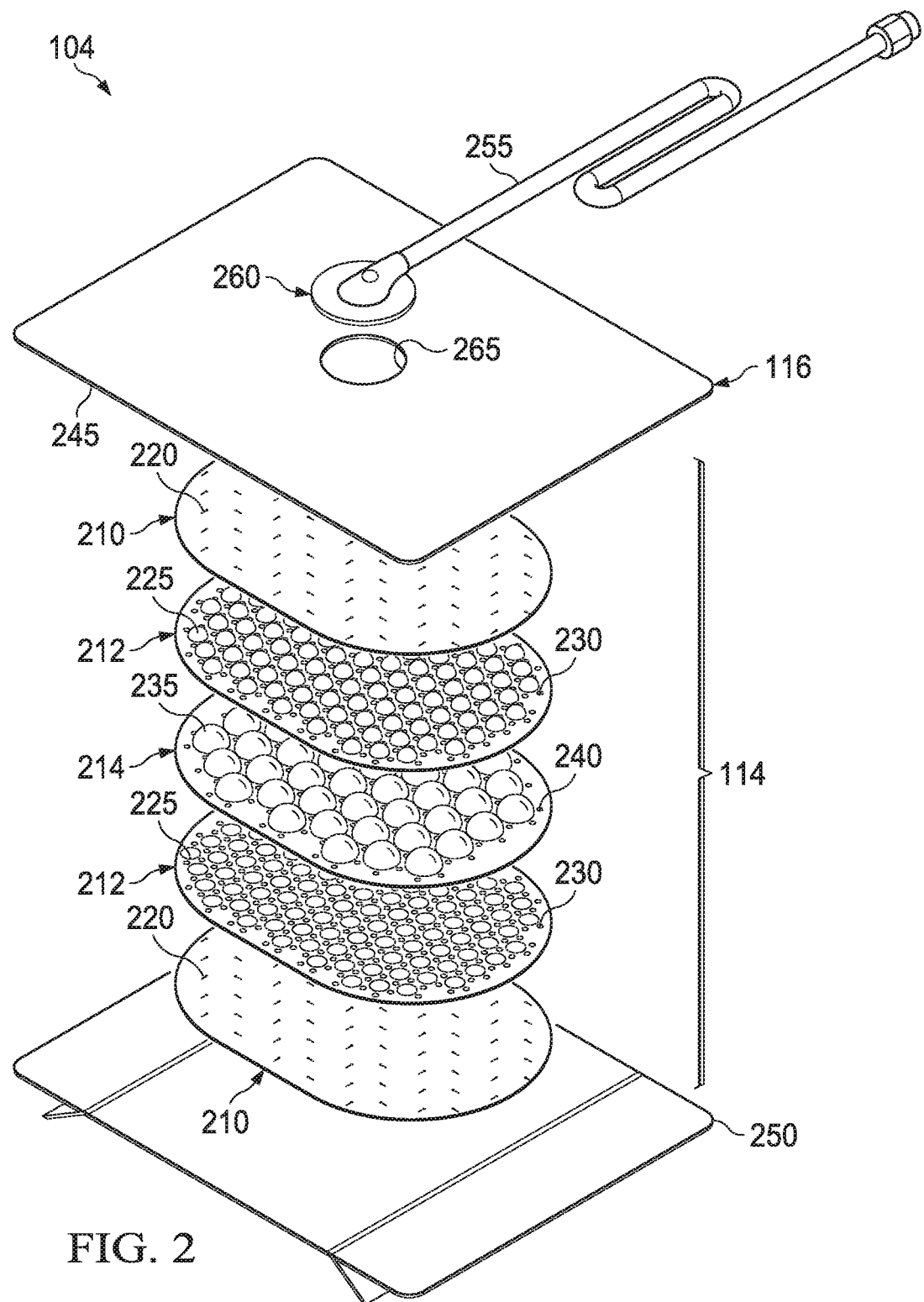
FIG. 2 is an assembly view of an example of a dressing, illustrating additional details that may be associated with some example embodiments of the therapy system of FIG. 1.

FIG. 2 is an assembly view of an example of the dressing 104 of FIG. 1, illustrating additional details that may be associated with some embodiments in which the tissue interface 114 comprises more than one layer. In the example of FIG. 2, the tissue interface 114 comprises a first layer 210, a second layer 212, and a third layer 214. In some embodiments, the third layer 214 may be disposed between portions of the second layer 212 and may also be disposed between portions of the first layer 210. For example, the second layer 212 may be disposed adjacent to two sides of the third layer 214. In some embodiments, for example, the second layer 212 may be laminated or otherwise mechanically bonded to two sides of the third layer 214. Additionally, the first layer 210 may be disposed adjacent to two sides of the second layer 212, and in some embodiments, the first layer 210 may be laminated or otherwise bonded to two sides of the second layer 212. The first layer 210, the second layer 212, and the third layer 214 may be stacked so that the second layer 212 is adjacent to and in contact with the first layer 210 and the third layer 214. The second layer 212 may also be bonded to the first layer 210, the third layer 214, or both in some embodiments. In some embodiments, the first layer 210 may form a sleeve or envelope around the second layer 212, the third layer 214, or both.

The first layer 210 may comprise or consist essentially of a means for controlling or managing fluid flow. In some embodiments, the first layer 210 may comprise or consist essentially of a liquid-impermeable, elastomeric material. For example, the first layer 210 may comprise or consist essentially of a non-porous polymer film. The first layer 210 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the second layer may have a substantially flat surface, with height variations limited to 0.2 millimeters over a centimeter.

In some embodiments, the first layer 210 may be hydrophobic. The hydrophobicity of the first layer 210 may vary, but may have a contact angle with water of at least ninety degrees in some embodiments. In some embodiments, the first layer 210 may have a contact angle with water of no more than 150 degrees. For example, in some embodiments, the contact angle of the first layer 210 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the first layer 210 may be further enhanced with a hydrophobic coating of other materials, such as silicones and fluorocarbons, either as coated from a liquid or plasma coated.

The first layer 210 may also be suitable for welding to other layers, including the second layer 212. For example, the first layer 210 may be adapted for welding to other film layers using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials such as polyethylene.

The area density of the first layer 210 may vary according to a prescribed therapy or application. In some embodiments, an area density of less than 40 grams per square meter may be suitable, and an area density of about 20-30 grams per square meter may be particularly advantageous for some applications.

In some embodiments, for example, the first layer 210 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. Films may be clear, colored, or printed. More polar films suitable for laminating to a polyethylene film include polyamide, copolyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the first layer 210 may have one or more fluid restrictions 220, which can be distributed uniformly or randomly across the first layer 210. The fluid restrictions 220 may be bi-directional and pressure-responsive. For example, each of the fluid restrictions 220 generally may comprise or consist essentially of an elastic passage that is normally unstrained to substantially reduce liquid flow, and can expand or open in response to a pressure gradient. In some embodiments, the fluid restrictions 220 may comprise or consist essentially of perforations in the first layer 210. Perforations may be formed by removing material from the first layer 210. For example, perforations may be formed by cutting through the first layer 210, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the first layer 210 may be a suitable valve for some applications. Fenestrations may also be formed by removing material from the first layer 210, but the amount of material removed and the resulting dimensions of the fenestrations may be an order of magnitude less than perforations, and may result in edges that are not deformed. Additionally, in some embodiments, perforations may be formed by mechanical slitting then controlled uni- and/or bi-axial stretching of the film material of the first layer 210.

For example, some embodiments of the fluid restrictions 220 may comprise or consist essentially of one or more slits, slots, or combinations of slits and slots in the first layer 210. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, ultrasonics, or other heat means, for example. The linear slits or slots may be spaced apart by about 2 to 4 millimeters along their length and from side-to-side. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

The second layer 212 generally comprises or consists essentially of a manifold or a manifold layer, which provides a means for collecting or distributing fluid across the tissue interface 114 under pressure. For example, the second layer 212 may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 114.

In some embodiments, the second layer 212 may comprise or consist essentially of a film of fluid-impermeable material having blisters 225. Polyurethane is an example of a suitable fluid-impermeable material for some applications of the second layer 212. In some embodiments, the blisters 225 may comprise a plurality of raised formations that extend above or below a plane of the second layer 212. Within each of the blisters 225 may be an empty cavity which may be open to the surrounding environment. For example, portions of a film of fluid-impermeable material that forms the second layer 212 may be shaped or formed into the blisters 225. In some embodiments, the blisters 225 may be in the form of small vacuum-formed regions of the film of the second layer 212. In some embodiments, each individual blister of the blisters 225 may be dome-shaped or hemispherically-shaped. Additionally or alternatively, the blisters 225 may be in the form of raised formations having different shapes, such as generally conical, cylindrical, tubular having a flattened or hemispherical end, or geodesic. The second layer 212 may further include apertures 230 to allow fluid transfer through the film. The blisters 225 may assist with enabling the second layer 212 to function as the core manifolding layer of the tissue interface 114.

The thickness of the second layer 212 may also vary according to needs of a prescribed therapy. For example, the thickness of the second layer 212 may be decreased to relieve stress on other layers and to reduce tension on peripheral tissue. The thickness of the second layer 212 can also affect the conformability of the second layer 212. In some embodiments, the second layer 212 may comprise a film having a thickness in a range of about 20 to 500 micrometers with blisters 225 having a diameter of between 0.5 mm and 2.0 mm. Depending on the particular embodiment, the orientation of the second layer 212 may be reversed so that the blisters 225 of the second layer 212 may either face or extend away from the first layer 210.

The third layer 214 may also comprise or consist essentially of a manifold. In some illustrative embodiments, the third layer 214 may comprise sealed regions defining a plurality of closed cells 235. In some embodiments, the closed cells 235 may be filled with fluid such as air. The third layer 214 may additionally comprise apertures 240 between the closed cells 235 to allow fluid transfer through the third layer 214. As mentioned with respect to the second layer 212, the orientation of the third layer 214 may be reversed.

The closed cells 235 are preferably resistant to collapsing under therapeutic levels of negative pressure. In some embodiments, closed cells 235 may be formed by a material have sufficient tensile strength to resist stretching under apposition forces of negative pressure. The tensile strength of a material is the ability of material to resist stretching as represented by a stress-strain curve where stress is the force per unit area, i.e., pascals (Pa), newtons per square meter ($N/m^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high-density polyethylene (HDPE) has a high tensile strength and low-density polyethylene (LDPE) has a slightly lower tensile strength, both of which are suitable materials for forming the closed cells 235. Linear low-density polyethylene (LLDPE) may be used as well because the material stretches very little as the force is increased up to the yield point of the material. The yield strength of HDPE ranges from 26-33 MPa, and has a UTS of 37 MPa, while LDPE has somewhat lower values. In some example embodiments, the closed cells 235 may be formed from a material that has a yield strength greater than about 20 MPa.

In the example of FIG. 2, the dressing 104 may further include an attachment device, such as an adhesive 245. The adhesive 245 may be, for example, a medically-acceptable, pressure-sensitive adhesive that extends about a periphery, a portion, or the entire cover 116. In some embodiments, for example, the adhesive 245 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 245 may be continuous or discontinuous. Discontinuities in the adhesive 245 may be provided by apertures or holes (not shown) in the adhesive 245. The apertures or holes in the adhesive 245 may be formed after application of the adhesive 245 or by coating the adhesive 245 in patterns on a carrier layer such as a side of the cover 116. Apertures or holes in the adhesive 245 may also be sized to enhance the MVTR of the dressing 104 in some example embodiments.

As illustrated in the example of FIG. 2, in some embodiments, the dressing 104 may include a release liner 250 to protect the adhesive 245 prior to use. The release liner 250 may also provide stiffness to assist with, for example, deployment of the dressing 104. The release liner 250 may be, for example, a casting paper, a film, or polyethylene. Further, in some embodiments, the release liner 250 may be a polyester material such as polyethylene terephthalate (PET) or similar polar semi-crystalline polymer. The use of a polar semi-crystalline polymer for the release liner 250 may substantially preclude wrinkling or other deformation of the dressing 104. For example, the polar semi-crystalline polymer may be highly orientated and resistant to softening, swelling, or other deformation that may occur when brought into contact with components of the dressing 104 or when subjected to temperature or environmental variations, or sterilization. Further, a release agent may be disposed on a side of the release liner 250 that is configured to contact the first layer 210. For example, the release agent may be a silicone coating and may have a release factor suitable to facilitate removal of the release liner 250 by hand and without damaging or deforming the dressing 104. In some embodiments, the release agent may be a fluorocarbon or a fluorosilicone, for example. In other embodiments, the release liner 250 may be uncoated or otherwise used without a release agent.

FIG. 2 also illustrates one example of a fluid conductor 255 and a dressing interface 260. As shown in the example of FIG. 2, the fluid conductor 255 may be a flexible tube, which can be fluidly coupled on one end to the dressing interface 260. The dressing interface 260 may be an elbow connector, as shown in the example of FIG. 2, which can be placed over an aperture 265 in the cover 116 to provide a fluid path between the fluid conductor 255 and the tissue interface 114.

In some embodiments of the dressing 104, one or more components of the dressing 104 may additionally be treated with an antimicrobial agent. For example, the first layer 210, the second layer 212, and/or the third layer 214 may be coated with an antimicrobial agent. In some embodiments, the first layer 210 may comprise a polymer coated or mixed with an antimicrobial agent. In further embodiments, the second layer 212 and the third layer 214 may comprise films coated or mixed with an antimicrobial agent. In other examples, the cover 116, the fluid conductor 255, the dressing interface 260, or other portion of the dressing 104 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Figure 3:
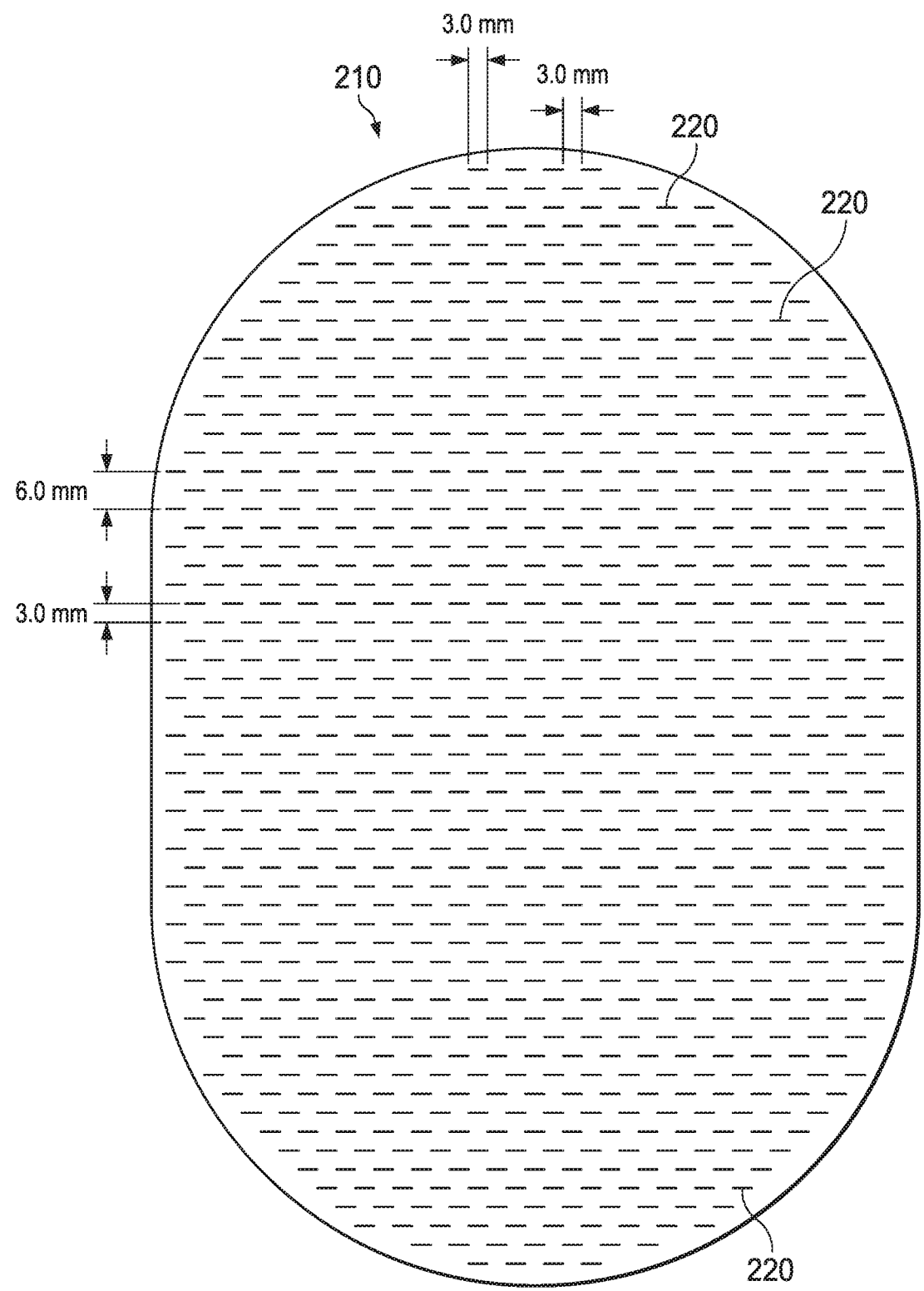
FIG. 3 is a schematic view of an example configuration of fluid restrictions in a layer that may be associated with some embodiments of the dressing of FIG. 2.

FIG. 3 is a schematic view of an example of the first layer 210, illustrating additional details that may be associated with some embodiments. As illustrated in the example of FIG. 3, the fluid restrictions 220 may each consist essentially of one or more linear slots having a length of about 3 millimeters. FIG. 3 additionally illustrates an example of a uniform distribution pattern of the fluid restrictions 220. In FIG. 3, the fluid restrictions 220 are substantially coextensive with the first layer 210 and are distributed across the first layer 210 in a grid of parallel rows and columns, in which the slots are also mutually parallel to each other. In some embodiments, the rows may be spaced about 3 millimeters on center, and the fluid restrictions 220 within each of the rows may be spaced about 3 millimeters on center as illustrated in the example of FIG. 3. The fluid restrictions 220 in adjacent rows may be aligned or offset. For example, adjacent rows may be offset, as illustrated in FIG. 3, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

Figure 4:
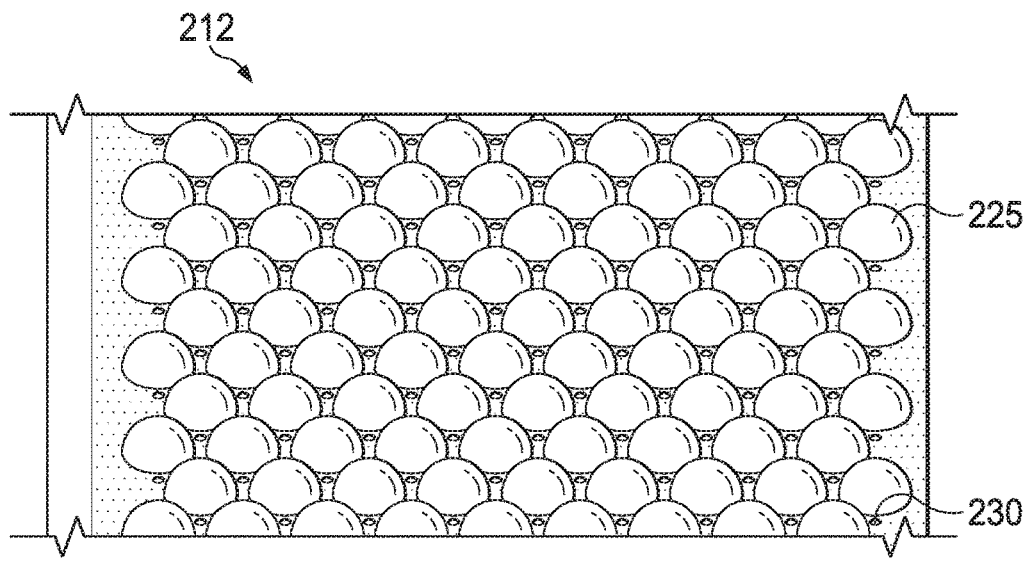
FIG. 4 is a top view of an example configuration of blisters in another layer that may be associated with some embodiments of the dressing of FIG. 2.

FIG. 4 is a perspective view of an example of the second layer 212, illustrating additional details that may be associated with some embodiments. As illustrated in the example of FIG. 4, the blisters 225 may be generally hemispherical and uniformly distributed in some embodiments.

Figure 5:
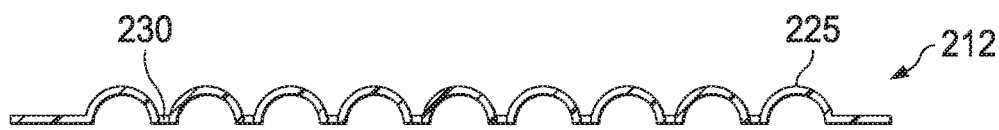
FIG. 5 is a section view illustrating additional details that may be associated with some embodiments of the layer of FIG. 4.

FIG. 5 is a section view of the second layer 212 of FIG. 4, illustrating additional details that may be associated with some embodiments. For example, the second layer 212 may be formed of a single sheet or film of fluid-impermeable material, which may have the blisters 225 and apertures 230 formed thereon. In some embodiments, the second layer 212 may be formed from a polyurethane material. The blisters 225 may be formed in the second layer 212 by applying a vacuum to the film of fluid-impermeable material of the second layer 212 to create the blisters 225. The blisters 225 may have dimensions that depend on the particular application of the dressing 104. For example, each of the blisters 225 may have a height between approximately 1.0 mm and 3.0 mm and may have a diameter between approximately 1.0 mm and 3.0 mm. In some embodiments, the blisters 225 may measure approximately 1.5 mm in height and approximately 1.5 mm in diameter. The distance between each of the blisters 225 may be between approximately 1.0 mm and 3.0 mm, and in some embodiments may have a spacing of approximately 2.0 mm.

As shown in FIG. 5, the apertures 230 may be formed in the portions of the second layer 212 that are between the blisters 225 and may extend through the film of fluid-impermeable material to permit fluids to flow through the second layer 212. The number of apertures 230 may vary depending on the type of negative pressure and instillation therapy to be provided by the therapy system 100. The apertures 230 may have different shapes, such as, for example, circular, elliptical, rectangular, or other irregular shape. Such apertures 230 may have a diameter, major axis, or length between about 0.5 mm and 1.5 mm. In some example embodiments, the apertures 230 may be formed by cutting or perforating the fluid-impermeable material of the second layer 212.

Figure 6:
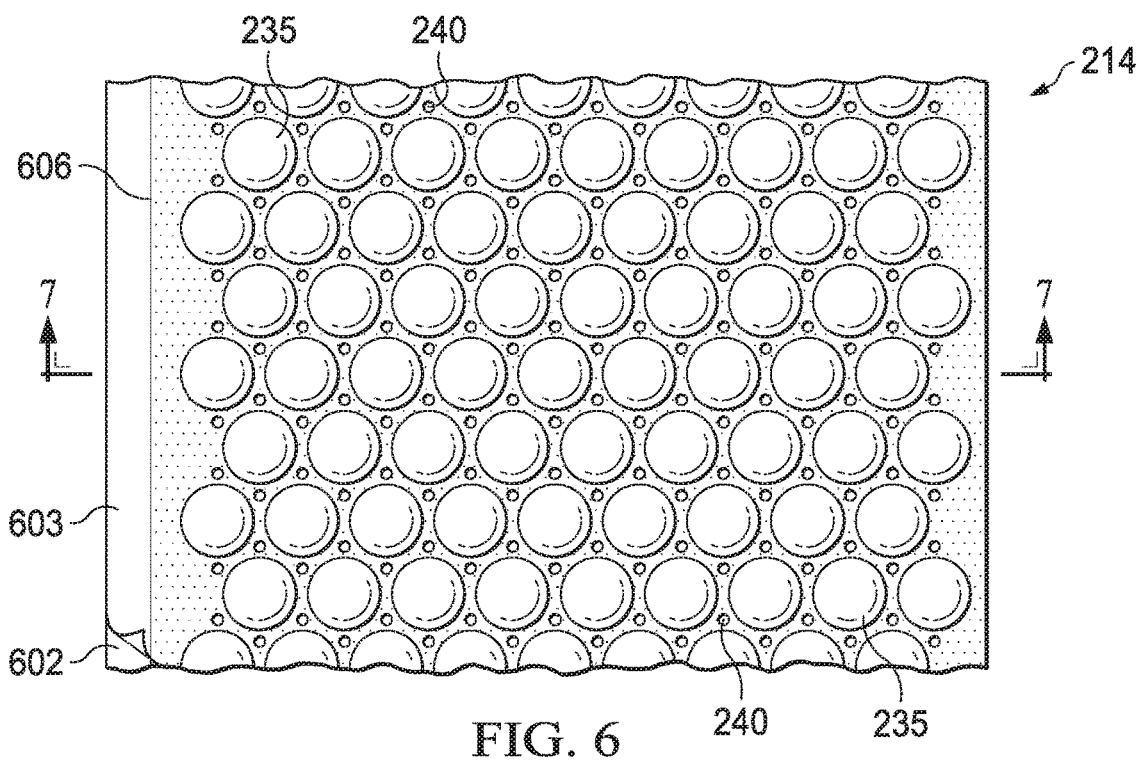
FIG. 6 is a top view of an example configuration of closed cells in another layer that may be associated with some embodiments of the dressing of FIG. 2.

FIG. 6 is a schematic view of an example of the third layer 214, illustrating additional details that may be associated with some embodiments. The third layer 214 may include a first sheet 602 and a second sheet 603 in some embodiments. For example, each of the first sheet 602 and the second sheet 603 may comprise or consist essentially of a non-porous polymer film, having inner surfaces coupled to each other to form a sealed region 606 defining a plurality of closed cells 235. The inner surfaces may be coupled to each other to form closed cells 235 that are substantially airtight to inhibit excessive collapsing of the closed cells 235 from the application of negative pressure, which could block the flow of fluid through the third layer 214.

The two sheets of non-porous, polymeric film, first sheet 602 and second sheet 603, may be in the form of a single sheet of material having two laminae or two separate sheets that are coupled together to form the closed cells 235. The sheets of non-porous, polymeric film may initially be separate sheets that are brought into superposition and sealed or they may be formed by folding a single sheet unto itself with a heat sealable surface facing inward. Each sheet of the non-porous polymeric film also may be a monolayer or multilayer structure depending on the application of the desired structure of the closed cells 235.

The sheets of non-porous, polymeric film may comprise any flexible material that can be manipulated to enclose closed cells. For example, the third layer 214 may be formed of two welded layers of polyolefin film that encapsulates air in pockets. Additionally or alternatively, various thermoplastic materials may be used for producing the film layers of the third layer 214. Non-limiting examples of suitable thermoplastic polymers include polyethylene homopolymers, such as low density polyethylene (LDPE) and high density polyethylene (HDPE), and polyethylene copolymers, such as, ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, and methyl pentene, in which the polymer molecules comprise long chains with relatively few side chain branches, including linear low-density polyethylene (LLDPE), linear medium-density polyethylene (LMDPE), very low-density polyethylene (VLDPE), and ultra-low-density polyethylene (ULDPE). Various other materials are also suitable such as, polypropylene homopolymer or polypropylene copolymer (e.g., propylene/ethylene copolymer), polyesters, polystyrenes, polyamides, polycarbonates, etc.

In some example embodiments, the sealed region 606 may be formed by a heat seal between the inner surfaces of sheet 602 and sheet 603. Additionally or alternatively, the sealed region 606 may be formed by adhesion between the sheet 602 and the sheet 603. The sheet 602 and sheet 603 may also be adhesively bonded to each other. The closed cells 235 may be substantially airtight when formed and have an internal pressure that is substantially an ambient pressure. In other embodiments, the closed cells 235 may be inflated with air or other suitable gas, such as, for example, carbon dioxide or nitrogen. The closed cells 235 may be inflated to have an internal pressure greater than the atmospheric pressure to maintain their shape and resistance to collapsing under pressure. For example, the closed cells 235 may be inflated to a pressure up to about 25 psi above the atmospheric pressure so that they do not collapse.

The sealed region 606 comprises sealed segments between the closed cells 235 that may be flexible enough so that the third layer 214 is sufficiently flexible to conform to the shape of the tissue site. The sealed segments may be sufficiently flexible or sized so that the third layer 214 may be folded into two or more layers. The sealed segments of the sealed region 606 may serve as common boundaries between adjacent closed cells 235. The sealed segments of the sealed region 606 may also be perforated to provide pathways for fluid to flow through the third layer 214. In some example embodiments, the sealed region 606 may include a plurality of apertures 240 between the closed cells 235 in the sealed region 606 and extending through both the sheet 602 and the sheet 603 to permit fluid to flow through the third layer 214. The number of apertures 240 may vary depending on the type of negative pressure and instillation therapy to be provided by the therapy system 100. The apertures 240 may have different shapes, such as, for example, circular, elliptical, rectangular, or other irregular shape. Such apertures 240 may have a diameter, major axis, or length between about 0.5 mm and 1.5 mm. In other example embodiment, the apertures 240 may be formed by perforating or cutting the segments of the sealed region 606.

As illustrated in the example of FIG. 6, the sealed region 606 may define the base or the cross-sectional shape of each of the closed cells 235 as generally circular. Additionally or alternatively, the base of one or more of the closed cells 235 may have other shapes, such as rectangular, triangular, or hexagonal. The closed cells 235 may be formed with a three-dimensional shape corresponding to the cross-sectional shape of the closed cells 235. For example, the volumetric shape may be generally hemispherical or spherical in shape as shown. In other example embodiments, the closed cells 235 may be formed with a volumetric shape that is generally conical, cylindrical, tubular having a flattened or hemispherical end, or geodesic shape. The closed cells 235 that are generally hemispherical or spherical in shape may have a diameter between about 0.5 mm and 10 mm. The closed cells 235 also may have a pitch, i.e., the center to center distance between each of the closed cells 235, between about 1.5 mm and 15 mm. Because the sealed region 606 defines the base of the closed cells 235 including the diameter of a circular base and the pitch of adjacent closed cells 235, the surface area of the third layer 214 covered by the closed cells 235 may also be determined as a percentage, i.e., the cell coverage percentage. In one example embodiment wherein the diameter of the closed cells 235 is about 1.0 mm and the pitch is about 2.0 mm, the cell coverage percentage is about 22% of the surface area of the third layer 214. In another example embodiment wherein the diameter of the closed cells 235 is about 2.0 mm and the pitch is about 5.0 mm, the cell coverage percentage is about 14% of the surface area of the third layer 214. In yet another example embodiment wherein the diameter of the closed cells 235 is about 1.0 mm and the pitch is about 1.5 mm, the cell coverage percentage is about 30% of the surface area of the third layer 214. In still another example embodiment wherein the diameter of the closed cells 235 is about 1.5 mm, the pitch is about 2.0 mm, and the closed cells 235 are more tightly arranged such that there are about 28.5 cells in a 10 mm$^2$ section of the third layer 214, the cell coverage percentage is about 51% of the surface area of the third layer 214. Depending on the diameter, pitch, and arrangement of the closed cells 235, the cell coverage percentage may range between about 10% and about 55% of the surface area of a manifold. Closed cells 235 having other base shapes or volumetric shapes also may have a cell coverage percentage in generally the same range.

Some embodiments of the closed cells 235 may have three-dimensional shapes, including hemispherical shapes, spherical shapes, conical shapes, cylindrical shapes, or tubular shapes formed with a flattened or hemispherical end. These shapes may be formed in one or both of sheet 602 and sheet 603, such as the single hemispherical shape shown in FIG. 7 (closed cells 704) and the two hemispherical shapes that are aligned with one another to form a spherical shape as shown in FIG. 8 (closed cells 804). The closed cells 235 may have a height between about 0.25 mm and about 5 mm, e.g., about half the diameter of closed cells 235 having a hemispherical shape as described in the examples above. In some embodiments, the closed cells 235 may measure about 10 mm in diameter and about 3 mm in height. In other example embodiments, the closed cells 235 may have a generally tubular shape formed with generally parallel walls extending from the sealed region 606 to a hemispherical end. In yet other example embodiments, closed cells 235 having a tubular shape may have a diameter of about 1.5 mm and an average height in a range between about 2.0 mm and 4.0 mm.

Still referring primarily to FIG. 6, the sheet 602 and the sheet 603 may each have a thickness of about 5 µm to 500 µm, and the sealed region 606 may have a thickness between about 10 µm and 1000 µm. The walls of the closed cells 235 after being formed by coupling the sheet 602 and the sheet 603 together may have a thickness relative to the thickness of the sheet 602 and the sheet 603 defined by a draw ratio, which is the ratio of the average height of the closed cells 235 to the average thickness of the sheet 602 and the sheet 603. In one example embodiment where the closed cells 235 have a generally tubular shape, the sheets 602 and 603 may have an average thickness of 250 µm and the closed cells 235 may have an average height in a range between about 2.0 mm and 4.0 mm with a diameter of about 1.5 mm. Consequently, the closed cells 235 have a draw ratio ranging from about 8:1 to about 16:1 for heights of 2.0 and 4.0 mm, respectively. In another example embodiment, the sheets 602 and 603 may have an average thickness of 100 µm and the closed cells 235 may have an average height in a range between about 2.0 mm and 4.0 mm with a diameter of about 1.5 mm. Consequently, the closed cells 235 have a draw ratio ranging from about 20:1 to about 40:1 for heights of 2.0 and 4.0 mm, respectively. In yet other example embodiments, it is desirable that the draw ratio be greater than about 16:1 where the thickness of the sheets 602 and 603 is less than about 250 µm. The sheets 602 and 603 may each have the same or different thicknesses and flexibilities, but are substantially non-stretchable as described above so that the closed cells 235 maintain a generally constant volume without bursting after negative pressure or instillation fluid is applied to the third layer 214. Consequently, even when a load is applied to the third layer 214 which squeezes closed cells 235 into a different shape, the closed cells 235 are sufficiently flexible to recover their original shape after being squeezed without bursting.

Figure 7:
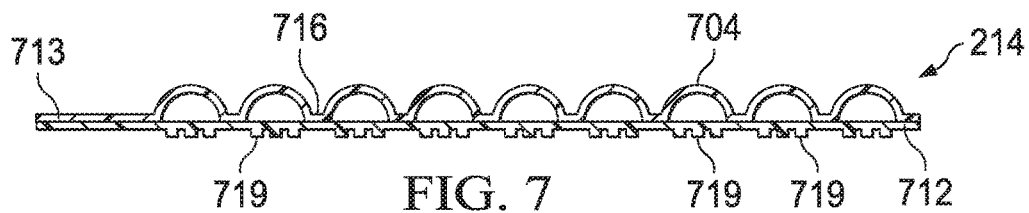
FIG. 7 is a section view illustrating additional details that may be associated with some embodiments of the layer of FIG. 6.
Figure 8:
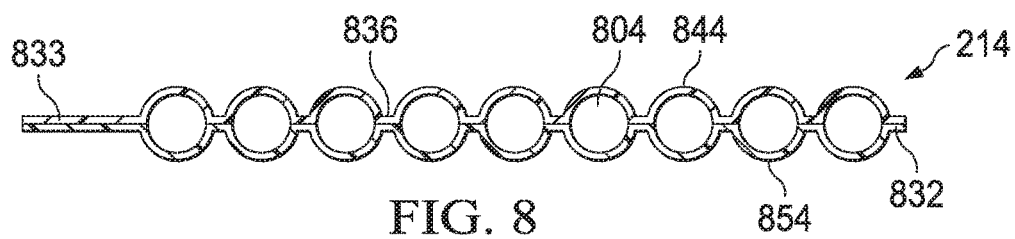
FIG. 8 is a section view illustrating additional details that may be associated with some embodiments of the layer of FIG. 6.

FIG. 7 is a section view of another example of the third layer 214, illustrating additional details that may be associated with some embodiments. For example, the third layer 214 of FIG. 7 may be configured so that the closed cells extend from only one side of the sealed region of the third layer 214, such as closed cells 704 having a hemispherical shape. More specifically, the third layer 214 may comprise two sheets of polymeric film, a first sheet 712 and a second sheet 713, having inner surfaces coupled to each other in a pattern defining a plurality of closed cells 704. The sheets 712 and 713 may be sealed to each other in a sealed region 716 that defines the closed cells 704 that are generally hemispherical in shape. The closed cells 704 may be formed on only one side of the sealed region 716 by using sheets of polymeric film having a different thickness or flexibility. For example, the closed cells 704 may be formed in the sheet 713 by applying a vacuum to the sheet 713 where the sheet 712 is sufficiently thicker than the sheet 713 to withstand the vacuum being applied and retain a generally planar shape. The closed cells 704 having other shapes may be formed to extend from only one side of the sealed region 716 and may be formed by using a variety of different methods. For example, the shape of the closed cells 704 may be formed separately in the sheet 713, which can be subsequently coupled to the sheet 712 to complete the encapsulation of the closed cells 704. The sheet 712 may have the same thickness as the sheet 713 so that the sealed region 716 remains thin and flexible.

In some embodiments, the third layer 214 may further include textured surface features on one or more surfaces of either or both of the sheets 712 and 713. The textured surface features may be included on a surface of either or both of the sheets 712 and 713 that may be placed facing the tissue site. The textured surface features may be protrusions or indentations for enhancing fluid flow through the third layer 214 and to increase micro-strains against the tissue site for enhancing granulation. More specifically, the textured surface features may include a pattern of individual nodes or projections embossed on the outer surface of the sheet 712 and/or sheet 713, a grid embossed on the outer surface of the sheet 712 and/or sheet 713, a pattern or grid of grooves formed into the outer surface of the sheet 712 and/or 713, or any combination of the foregoing. For example, as shown in FIG. 7, the third layer 214 may include textured surface features in the form of nodes 719, which may be embossed on the outer surface of the sheet 712 that is generally planar so that the nodes 719 contact the tissue site when the third layer 214 is positioned at the tissue site.

The nodes 719 may be projections that are flexible or rigid. In some embodiments, the projections may be formed from a substantially gas-impermeable material such as silicone. In other embodiments, the projections may be formed from a semi-gas-permeable material. The projections may be formed as an integral part of the sheets 712 and 713, and they may also be formed from the same material as the sheets 712 and 713. In some embodiments, the projections may be solid, while in other embodiments, the projections may be hollow to increase flexibility. The projections may form a plurality of channels and/or voids as described below to distribute negative pressure and allow for fluid flow among the projections. The projections may be dimensioned to provide local load points at a tissue site sufficient to create micro-strains at the tissue site for stimulating granulation formation when negative pressure is applied. The pattern and position of the projections may be uniform or non-uniform. The projections may have different shapes including, for example, the shape of a spike, cone, pyramid, dome, cylinder, or rectangle. The shapes of the projections may be uniform or non-uniform depending on the tissue site. The shapes of the projections may occupy a volume defined by a cube volume where the side of the cube would range from approximately 0.2 mm approximately 1.5 mm. In one embodiment, the spike shape may have a base width or diameter of about 0.2 mm and a vertical height of between about 0.4 mm and 0.8 mm. In another embodiment, the cone shape may have a base diameter of about 0.4 mm and a vertical height of between 0.4 mm to 1.2 mm. In yet another embodiment, the dome shape may have a spherical cap or parabolic shape with a base diameter ranging from about 0.4 mm to 1 mm.

FIG. 8 is a section view of another example of the third layer 214, illustrating additional details that may be associated with some embodiments. For example, the third layer 214 of FIG. 8 may include portions of closed cells that are formed in both of the two sheets of the third layer 214, so that the portions closed cells extend from both sides of the sealed region of the third layer 214. More specifically, the third layer 214 may comprise two sheets of polymeric film, sheet 832 and sheet 833, having inner surfaces coupled to each other in a pattern defining a plurality of closed cells 804. For example, the portions of closed cells formed in each of the sheets 832 and 833 may be hemispherical in shape, such as hemispherical cell 844 and hemispherical cell 854. The hemispherical cell 844 and hemispherical cell 854 may then be aligned to form a single closed cell 804 having a generally spherical shape. In other words, each of the single closed cells 804 comprises two hemispherical cells, hemispherical cell 844 and hemispherical cell 854, formed in the sheets 832 and 833, respectively. The sheets 832 and 833 may be sealed to each other in a sealed region 836 that defines the closed cells 804 that are generally spherical in shape. In other example embodiments, the closed cells in each sheet may not be aligned with each other, but rather are overlapped or aligned with the sealed portion of the opposite sheet. The closed cells 804 may be formed on both sides of the sealed region 836 by using sheets of polymeric film having a different thickness or flexibility. For example, the shape of the closed cells 804 may be asymmetric when the sheets 832 and 833 have different thicknesses or flexibilities from each other. However, when the sheets 832 and 833 have substantially identical thickness or flexibility, the shape of the closed cells 804 may be substantially spherical as shown in FIG. 8.

Figure 9:
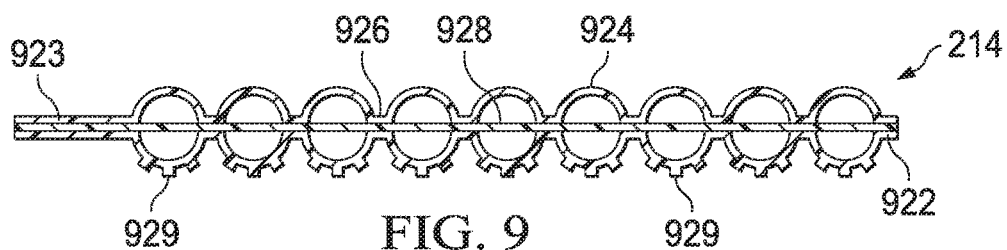
FIG. 9 is a section view illustrating additional details that may be associated with some embodiments of the layer of FIG. 6.

FIG. 9 is a section view of another example of the third layer 214, illustrating additional details that may be associated with some embodiments. For example, the third layer 214 of FIG. 9 may include a third sheet forming a multi-sheet configuration where the third sheet is disposed between a first sheet and a second sheet to form closed cells that may be generally spherical in shape formed by two hemispherical sections separated by portions of the third sheet of material. For example, the third layer 214 may include sheet 922 and sheet 923 of polymeric film having inner surfaces coupled or bonded to a third sheet 928 to form sealed region 926 defining a plurality of closed cells 924. The closed cells 924 are generally spherical in shape and formed by two hemispherical sections that are separated by portions of the third sheet 928. Sheet 922 and sheet 923 may be coupled or bonded to the third sheet 928 using a variety of different methods including, for example, melting (e.g., RF, ultrasonic, and heat), adhesives using both hot melt and solvents, and pressing techniques. The third sheet 928 may be formed from a polymeric film and may also be perforated to permit airflow between the two hemispherical sections of the closed cells 924. When the third sheet 928 is formed from a polymeric material, the third sheet 928 may also be textured to provide wicking capability. The third sheet 928 may also be formed from a polyester material to provide wicking within the closed cells 924 and may further include fibers flocked into the polyester material to provide additional wicking capability. The third sheet 928 may also include an antimicrobial layer or antimicrobials coated on the third sheet 928.

In some embodiments, the third layer 214 of FIG. 9 may also include textured surface features on one or more surfaces of either or both of the sheets 922 and 923. The textured surface features may be protrusions or indentations, as discussed with respect to the textured surface features of FIG. 7. For example, the third layer 214 may include projections or nodes 929 embossed on the outer surface of the sheet 922 and, more specifically, on the surface of the closed cells 924 so that the nodes 929 contact the tissue site if the third layer 214 is positioned at the tissue site.

Figure 10:
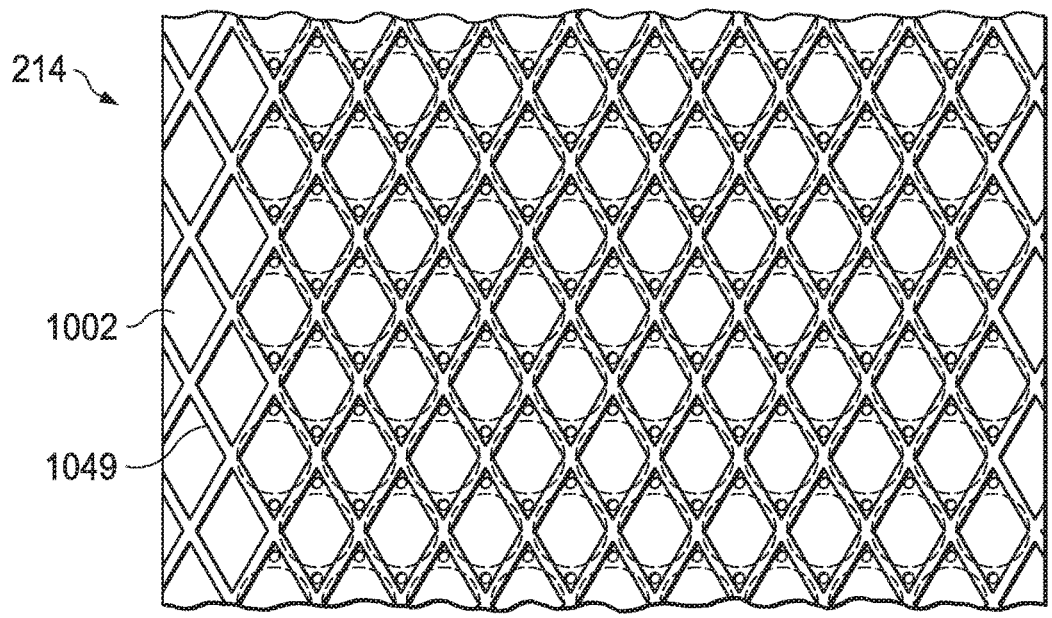
FIG. 10 is a top view of another example configuration of closed cells in a layer that may be associated with some embodiments of the dressing of FIG. 2.

FIG. 10 is a schematic view of another example of the third layer 214, illustrating additional details that may be associated with some embodiments. For example, a number of different textures or shapes may be formed on the outside surface of a first sheet 1002 that may be flat and may be for facing a tissue site when in use. In one exemplary embodiment, a grid 1049 may be embossed or extruded in a woven pattern on the outer surface of the first sheet 1002. The pattern of the grid 1049 may have a variety of shapes, like the diamond-shaped pattern shown. It should be understood that many types of protrusions or grids may be formed on a surface of the first sheet 1002 or a first sheet of other disclosed embodiments of the third layer 214 for enhancing fluid flow through or along the third layer 214 and/or enhance granulation of a tissue site. Moreover, it should be understood that any of such protrusions or grids may be formed by embossing, welding, or any other similar type of coupling mechanism.

Figure 11:
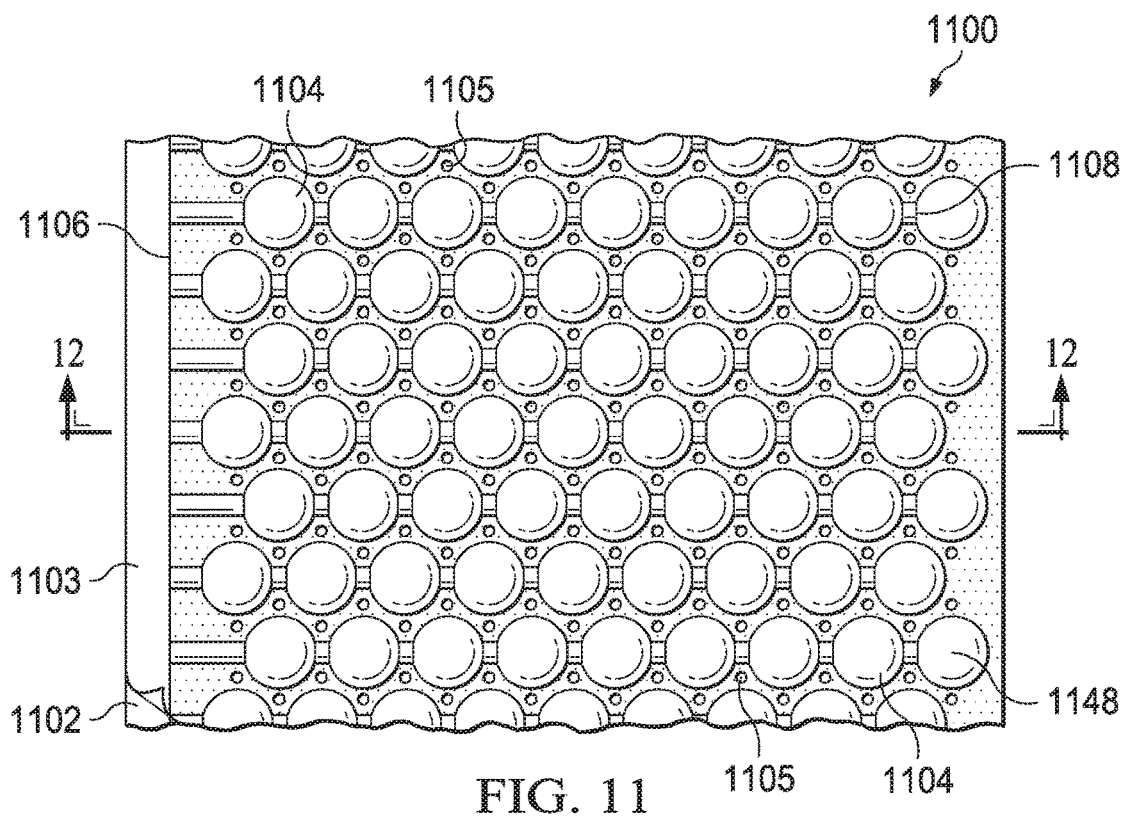
FIG. 11 is a top view of another example configuration of closed cells in a layer that may be associated with some embodiments of the dressing of FIG. 2.

FIG. 11 is a schematic view of another example of a third layer 1100, illustrating additional details that may be associated with some embodiments. The third layer 1100 may be similar to the embodiments of third layer 214 previously discussed but may further include chambers formed by interconnected closed cells to better distribute the apposition force applied to the third layer 1100 as a result of the application of negative pressure since the volume of the chambers is greater than the volume of the individual closed cells. In one embodiment, as shown in FIG. 11, the third layer 1100 includes a sheet 1102 and a sheet 1103, each of which may be a polymeric film having inner surfaces coupled to each other in a pattern defining a plurality of closed cells 1104. The sheets 1102 and 1103 may be sealed to each other to form a sealed region 1106 defining the closed cells 1104. The sealed region 1106 may also be perforated to provide pathways for fluid to flow through the third layer 1100. In one exemplary embodiment, the sealed region 1106 may comprise a plurality of apertures 1105 that are formed between the closed cells 1104 in the sealed region 1106 that extend through both of the sheets 1102 and 1103 to permit fluid flow through the third layer 1100. The third layer 1100 may also comprise a plurality of passageways 1108 fluidly coupling at least two of the closed cells 1104 to form a closed chamber. In one exemplary embodiment, a closed chamber 1148 is formed by all of the closed cells 1104 in a row fluidly coupled by the passageways 1108 as shown in FIG. 11. Closed chambers 1148 may be formed in each of the other six rows as also shown in FIG. 11. The formation of closed chambers with closed cells in any pattern may distribute apposition forces applied to the third layer 1100 more equally across the third layer 1100.

Figure 12:
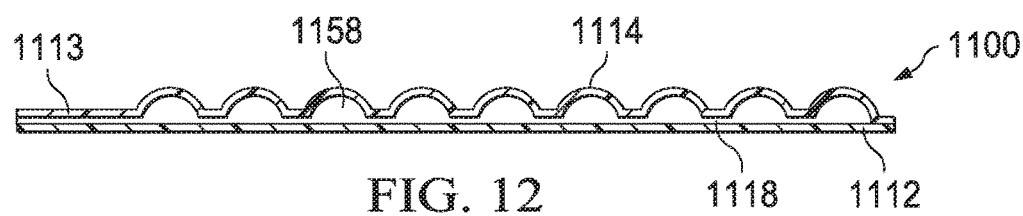
FIG. 12 is a section view illustrating additional details that may be associated with some embodiments of the layer of FIG. 11.

FIG. 12 is a section view of another example of the third layer 1100, illustrating additional details that may be associated with some embodiments. For example, the third layer 1100 of FIG. 12 may include two sheets of polymeric film, sheet 1112 and sheet 1113, having inner surfaces coupled to each other in a pattern defining a plurality of closed cells 1114. The sheets 1112 and 1113 may be sealed to each other in a sealed region that defines the closed cells 1114 that are generally hemispherical in shape. The third layer 1100 also may comprise a plurality of passageways 1118 interconnecting the closed cells 1114 to form a closed chamber 1158. The closed chamber 1158 may be formed in only one of the sheets 1112 and 1113 so that they extend from only one side of the sealed region as shown in FIG. 12.

Figure 13:
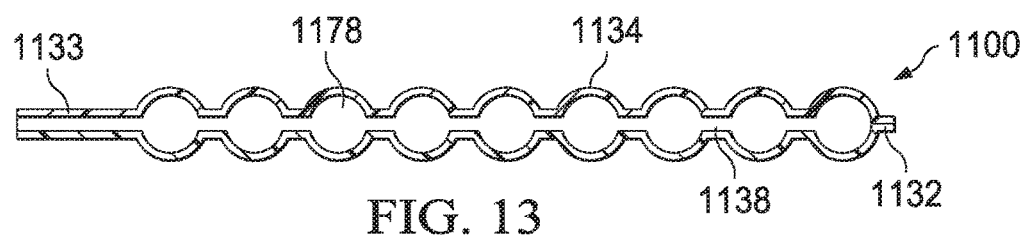
FIG. 13 is a section view illustrating additional details that may be associated with some embodiments of the layer of FIG. 11.

FIG. 13 is a section view of another example of the third layer 1100, illustrating additional details that may be associated with some embodiments. For example, the third layer 1100 of FIG. 13 may include two sheets of polymeric film, sheet 1132 and sheet 1133, having inner surfaces coupled to each other in a pattern defining a plurality of closed cells 1134. The sheets 1132 and 1133 may be sealed to each other in a sealed region that defines the closed cells 1134 that are generally spherical in shape. The third layer 1100 also may comprise a plurality of passageways 1138 interconnecting the closed cells 1134 to form a closed chamber 1178. The closed chamber 1178 is formed in both of the sheets 1132 and 1133 so that they extend from both sides of the sealed region that provides more flexibility and cushioning than the closed chamber 1158 extending from only one side of the sealed region.

Figure 14:
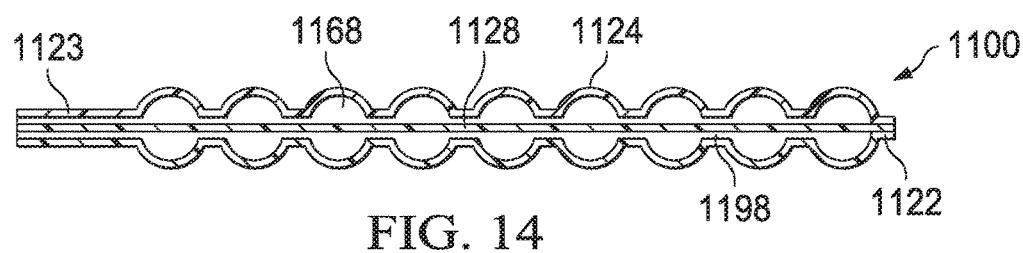
FIG. 14 is a section view illustrating additional details that may be associated with some embodiments of the layer of FIG. 11.

FIG. 14 is a section view of another example of the third layer 1100, illustrating additional details that may be associated with some embodiments. For example, the third layer 1100 of FIG. 14 may include two sheets of polymeric film, sheet 1122 and sheet 1123, having inner surfaces coupled or bonded to a third sheet 1128 to form a sealed region defining a plurality of closed cells 1124. The closed cells 1124 are generally spherical in shape and formed by two hemispherical sections that are separated by portions of the third sheet 1128. Sheet 1122 and sheet 1123 may be coupled or bonded to the third sheet 1128 using a variety of different methods including, for example, melting (e.g., RF, ultrasonic, and heat), adhesives using both hot melt and solvents, and pressing techniques. The third sheet 1128 may be formed from a polymeric film and may also be perforated to permit airflow between the two hemispherical sections of the closed cells 1124. When the third sheet 1128 is formed from a polymeric material, the third sheet 1128 may also be textured to provide wicking capability. The third sheet 1128 may also be formed from a polyester material to provide wicking within the closed cells 1124, and may further include fibers flocked into the polyester material to provide additional wicking capability. The third sheet 1128 also may include an antimicrobial layer or antimicrobials coated on the third sheet 1128. The third layer 1100 of FIG. 14 may also include a plurality of passageways 1198 interconnecting the closed cells 1124 to form a closed chamber 1168. The closed chamber 1168 is formed in both of the sheets 1122 and 1123 so that they extend from both sides of the sealed region.

Figure 15:
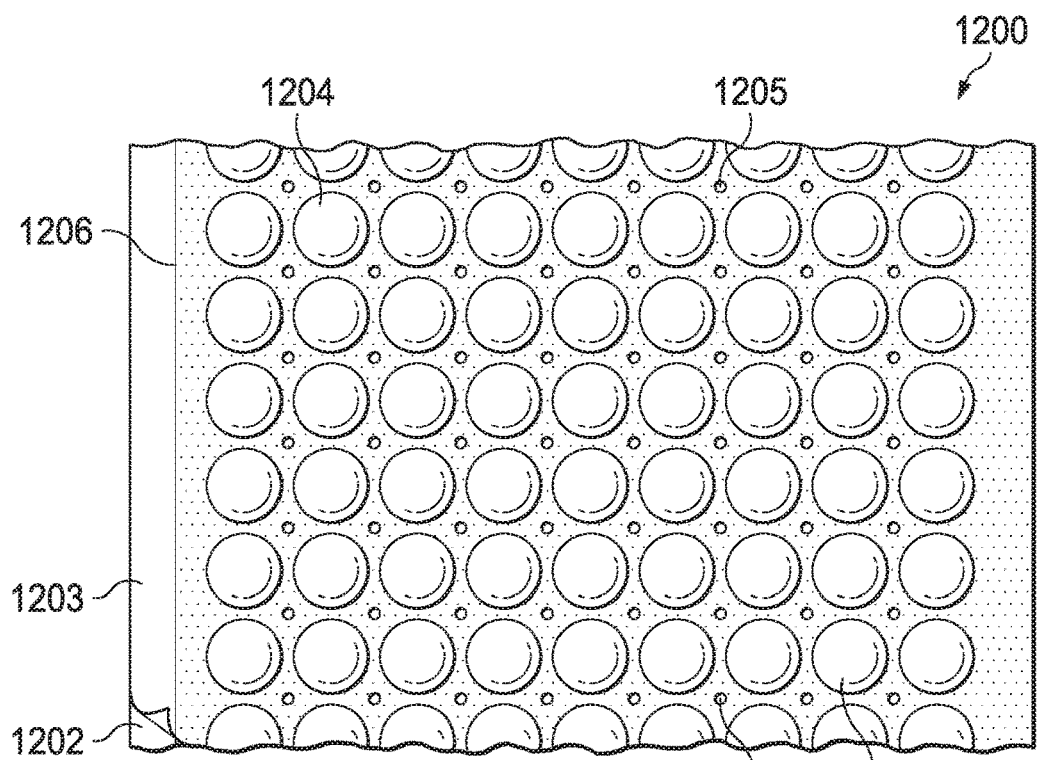
FIG. 15 is a top view of another example configuration of closed cells in a layer that may be associated with some embodiments of the dressing of FIG. 2.

FIG. 15 is a schematic view of another example of a third layer 1200, illustrating additional details that may be associated with some embodiments. The third layer 1200 may be similar to the embodiments of the third layer 214 previously discussed but may include different arrangements of closed cells, which may be suitable for particular forms of therapy being utilized. Previously discussed with respect to FIG. 6 were closed cells 235 which are in a staggered arrangement so that the individual cells may be more closely nested together between the alternating rows to form a nested pattern of cells formed on the same plane as defined by the sealed region 606. FIG. 15 depicts a third layer 1200 that may include two sheets 1202 and 1203 of polymeric film having inner surfaces sealed to each other in a pattern defining a plurality of closed cells 1204 in close proximity to one another. However, the rows and columns of closed cells 1204 are not staggered, but rather arranged in an aligned pattern. Depending on the diameter and pitch of the closed cells 1204, the cell coverage percentage may range between about 10% and about 55% of the surface area of the third layer 1200. The sheets 1202 and 1203 may be sealed to each other in a sealed region 1206 that defines the closed cells 1204. In this embodiment, the rows and columns of the closed cells 1204 are arranged in line to form an aligned pattern. The third layer 1200 may also include a sealed region 1206 that may be perforated as described above. In some embodiments, the sealed region 1206 may include a plurality of apertures 1205 between the closed cells 1204 and extending through both the sheet 1202 and the sheet 1203 to permit fluid to flow through the third layer 1200. The apertures 1205 may have similar dimensions as apertures 240 of FIG. 6. The pattern of closed cells 1204 may have a variety of arrangements.

Figure 16:
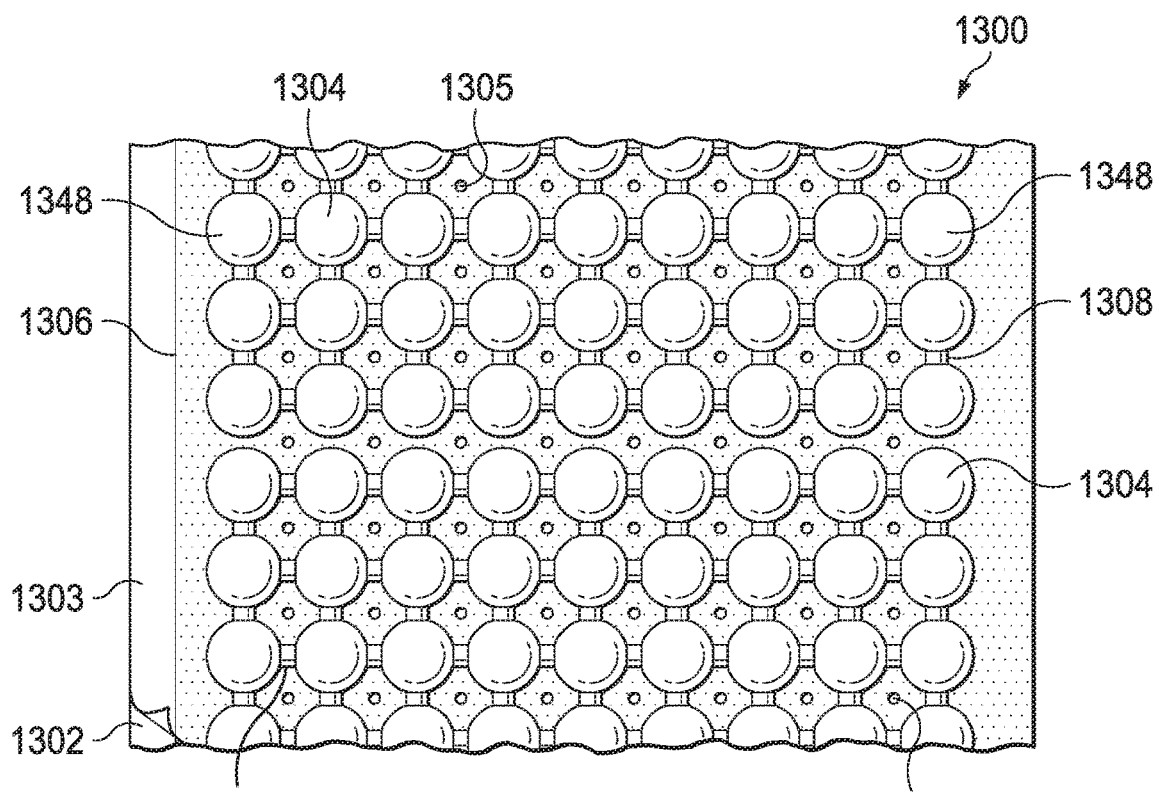
FIG. 16 is a top view of another example configuration of closed cells in a layer that may be associated with some embodiments of the dressing of FIG. 2.

FIG. 16 is a schematic view of another example of a third layer 1300, illustrating additional details that may be associated with some embodiments. The third layer 1300 may be similar to the third layer 1200 of FIG. 15 and may include two sheets 1302 and 1303 of polymeric film having inner surfaces sealed to each other in a pattern defining a plurality of closed cells 1304 in close proximity to one another. The sheets 1302 and 1303 may be sealed to each other in a sealed region 1306 that defines the closed cells 1304. The sealed region 1306 may also be perforated to provide pathways for fluid to flow through the third layer 1300. In one exemplary embodiment, the sealed region 1306 may comprise a plurality of apertures 1305 that are formed between the closed cells 1304 in the sealed region 1306 that extend through both of the sheets 1302 and 1303 to permit fluid flow through the third layer 1300. The third layer 1300 may also comprise a plurality of passageways 1308 interconnecting the closed cells 1304 to form a closed chamber. In one exemplary embodiment, a closed chamber 1348 is formed by all of the closed cells 1304 in a row fluidly coupled by the passageways 1308 as shown in FIG. 16. Closed chambers 1348 may be formed in each of the other six rows, or formed to include multiple rows, as also shown in FIG. 16. The formation of closed chambers 1348 with closed cells 1304 in any pattern may distribute apposition forces applied to the third layer 1300 more equally across the third layer 1300 as opposed to a layer having only closed cells.

Referring again primarily to FIG. 2, the individual components of the dressing 104 may be bonded or otherwise secured to one another with a solvent or non-solvent adhesive or with thermal welding, for example, without adversely affecting fluid management. For example, the layers of the tissue interface 114, such as the first layer 210, the second layer 212, and the third layer 214 may be laminated to each other. In some embodiments, a low-melting-point (approximately 60° C., for example) hot melt adhesive mesh may be applied to the bonding surfaces of any or all of the first layer 210, the second layer 212, and the third layer 214, prior to any perforations being made in the layers. The layers, which may be film layers, may then be laminated together under relatively low compression and heat application to soften the hot melt mesh in order to complete the bonding. Additionally or alternatively, the layers of the tissue interface 114 and dressing 104 may be welded together in an array or pattern such that a textured 'spot weld' pattern is formed using RF, ultrasonics, or heat.

The individual components of the dressing 104, such as the cover 116, the first layer 210, the second layer 212, and the third layer 214, or various combinations, may be assembled before application or in situ. For example, the cover 116 may be laminated to the first layer 210, and the second layer 212 may be laminated to the first layer 210 opposite the cover 116 in some embodiments. Additionally, the third layer 214 may be laminated to the second layer 212 opposite the first layer 210. In some embodiments, one or more layers of the tissue interface 114 may be coextensive. For example, the first layer 210, the second layer 212, and the third layer 214 may be cut flush with the edges of each other, thus exposing the edges of all three layers. In other embodiments, any one of the first layer 210, the second layer 212, and the third layer 214 may overlap the edge of any of the other layers. In some embodiments, the dressing 104 may be provided as a single, composite dressing. For example, the second layer 212 and the third layer 214 may be positioned between portions of the first layer 210, where a portion of the first layer 210 may be coupled to the cover 116 and another portion of the first layer 210 may be configured to face a tissue site.

In use, the release liner 250 (if included) may be removed to expose the first layer 210, which may be placed within, over, on, or otherwise proximate to a tissue site, particularly a surface tissue site, and adjacent epidermis. The first layer 210 may be interposed between the second layer 212 and the tissue site and adjacent epidermis, which can substantially reduce or eliminate interaction with the second layer 212 or third layer 214. For example, the first layer 210 may be placed over a surface wound (including edges of the wound) and undamaged epidermis. Treatment of a surface wound or placement of the dressing 104 on a surface wound includes placing the dressing 104 immediately adjacent to the surface of the body or extending over at least a portion of the surface of the body. Treatment of a surface wound may not include placing the dressing 104 wholly within the body or wholly under the surface of the body. The cover 116 may be sealed to an attachment surface, such as epidermis peripheral to a tissue site, around the first layer 210, the second layer 212, and the third layer 214.

The geometry and dimensions of the tissue interface 114, the cover 116, or both may vary to suit a particular application or anatomy. For example, the geometry or dimensions of the tissue interface 114 and the cover 116 may be adapted to provide an effective and reliable seal against challenging anatomical surfaces, such as an elbow or heel, at and around a tissue site. Additionally or alternatively, the dimensions may be modified to increase the surface area for the first layer 210 to enhance the movement and proliferation of epithelial cells at a tissue site and reduce the likelihood of granulation tissue in-growth.

Further, the dressing 104 may permit re-application or re-positioning to reduce or eliminate leaks, which can be caused by creases and other discontinuities in the dressing 104 or a tissue site. The ability to rectify leaks may increase the reliability of the therapy and reduce power consumption in some embodiments.

Thus, the dressing 104 in the example of FIG. 2 can provide a sealed therapeutic environment proximate to a tissue site, substantially isolated from the external environment, and the negative-pressure source 102 can reduce the pressure in the sealed therapeutic environment. Negative pressure in the sealed environment may compress the second layer 212 and/or the third layer 214 into the first layer 210, which can deform the surface of the first layer 210 to provide an uneven, coarse, or jagged profile that can induce macrostrain and micro-strain in the tissue site in some embodiments.

If not already configured, the dressing interface 260 may be disposed over the aperture 265 and attached to the cover 116. The fluid conductor 255 may be fluidly coupled to the dressing interface 260 and to the negative-pressure source 102.

Negative pressure applied through the tissue interface 114 can create a negative pressure differential across the fluid restrictions 220 in the first layer 210, which can open or expand the fluid restrictions 220. For example, in some embodiments in which the fluid restrictions 220 may comprise perforations through the first layer 210, a pressure gradient across the perforations can strain the adjacent material of the first layer 210 and increase the dimensions of the perforations to allow liquid movement through them, similar to the operation of a duckbill valve. Opening the fluid restrictions 220 can allow exudate and other liquid movement through the fluid restrictions 220 into the second layer 212, the third layer 214, and the container 106. If the negative-pressure source 102 is removed or turned-off, the pressure differential across the fluid restrictions 220 can dissipate, allowing the fluid restrictions 220 to return to an unstrained or resting state and prevent or reduce the return rate of exudate or other liquid moving to the tissue site through the first layer 210.

Additionally or alternatively, instillation solution or other fluid may be distributed to the dressing 104, which can increase the pressure in the tissue interface 114. The increased pressure in the tissue interface 114 can create a positive pressure differential across the fluid restrictions 220 in the first layer 210, which can open or expand the fluid restrictions 220 from their resting state to allow the instillation solution or other fluid to be distributed to the tissue site.

Figure 17:
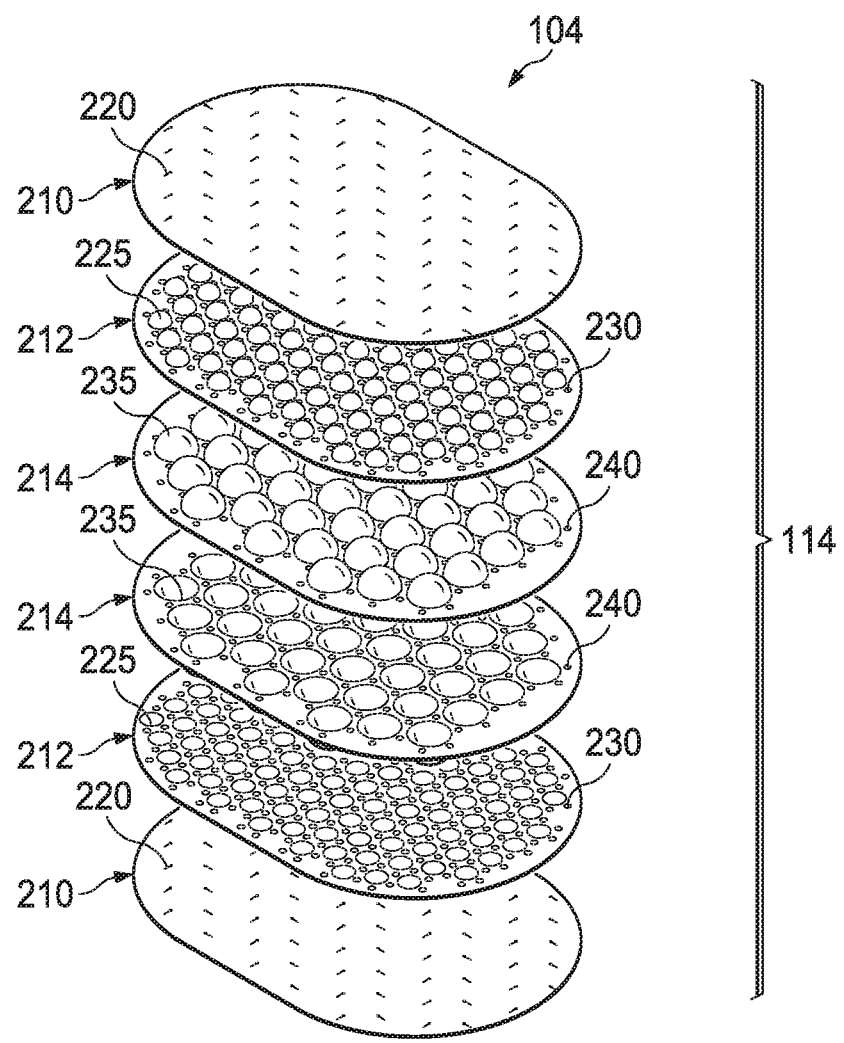
FIG. 17 is an assembly view of an example of a tissue interface, illustrating additional details that may be associated with some example embodiments of the therapy system of FIG. 1.

FIG. 17 is an assembly view of another example of the tissue interface 114 of FIG. 1, illustrating additional details that may be associated with some embodiments. In the example of FIG. 17, the third layer 214 may be disposed between the second layer 212 and may also be disposed between the first layer 210. In the example of FIG. 17, the third layer 214 may include two separate layers, with each of the separate layers including closed cells. Additional layers of closed cells in the third layer 214 may increase the conformable compression feel to the tissue interface 114. The two separate layers of closed cells can be positioned proximate to or against each other. The two layers of the third layer 214 may be positioned between the second layer 212, with the second layer 212 positioned adjacent to two sides of the third layer 214. In some embodiments, for example, the second layer 212 may be laminated or otherwise mechanically bonded to two sides of the third layer 214. Additionally, the first layer 210 may be disposed adjacent to two sides of the second layer 212, and in some embodiments, the first layer 210 may be laminated or otherwise bonded to two sides of the second layer 212. The first layer 210, the second layer 212, and the third layer 214 may be stacked so that the second layer 212 is adjacent to and in contact with the first layer 210 and the third layer 214. The second layer 212 may also be bonded to the first layer 210, the third layer 214, or both in some embodiments.

In the embodiment of FIG. 17, each of the two separate layers of the third layer 214 may be oriented so that the closed cells 235 of each of the separate layers are facing opposite directions from each other. For example, the closed cells 235 on a first of the two layers of the third layer 214 may be facing or protruding upwards towards a first side of the tissue interface 114, while the closed cells 235 of a second of the two layers of the third layer 214 may be facing or protruding downwards towards a second side of the tissue interface 114. In other embodiments (not shown), the two layers of the third layer 214 may be oriented so that the closed cells are facing each other. For example, the third layer 214 may include two layers having hemispherical closed cells which face each other.

Figure 18:
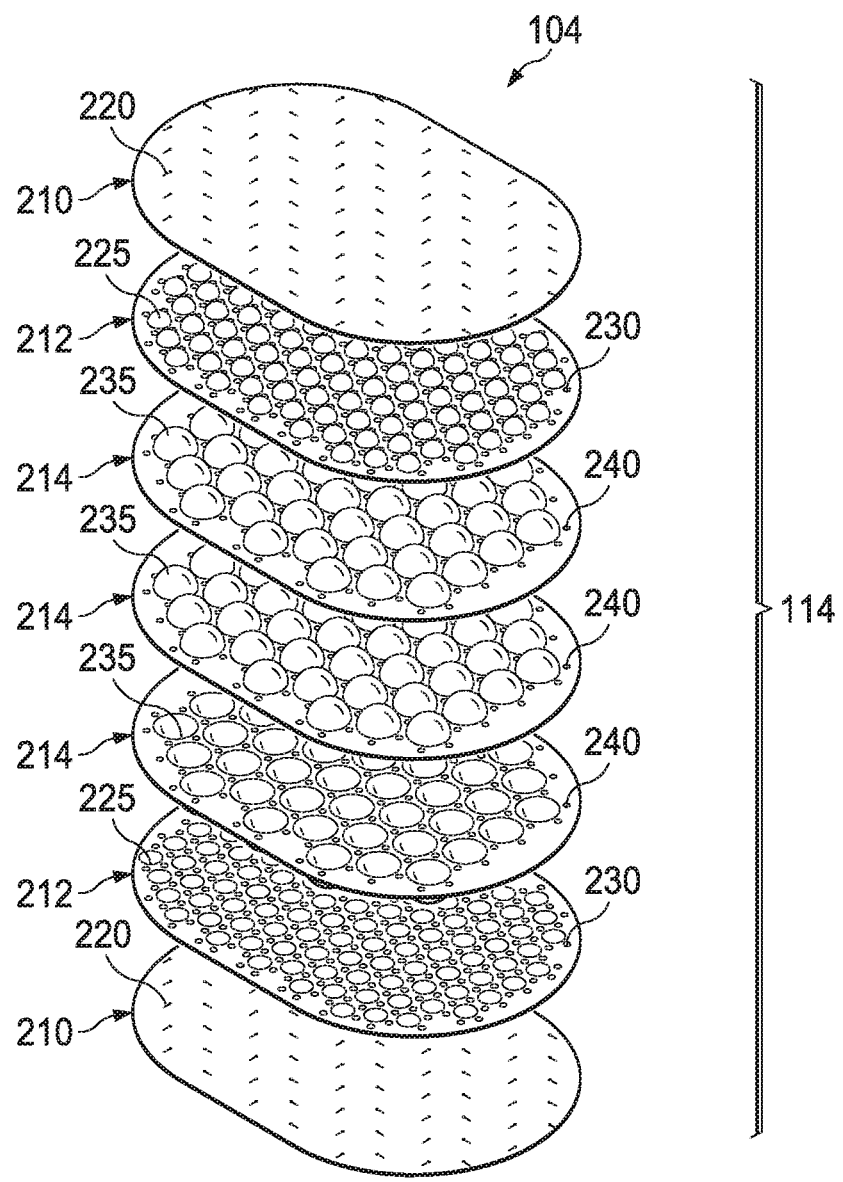
FIG. 18 is an assembly view of another example of a tissue interface, illustrating additional details that may be associated with some example embodiments of the therapy system of FIG. 1.

FIG. 18 is an assembly view of another example of the tissue interface 114 of FIG. 1, illustrating additional details that may be associated with some embodiments. The tissue interface 114 of FIG. 18 may be similar to the tissue interface 114 of FIG. 17, with the exception of the third layer 214 comprising three separate layers that may be positioned proximate to or against each other. The three separate layers of the third layer 214 may be positioned between the second layer 212, which may be positioned between the first layer 210. In the embodiment of FIG. 18, the three separate layers of the third layer 214 may be oriented so that the closed cells 235 of a first and second layers of the third layer 214 may be facing or protruding upwards towards a first side of the tissue interface 114, while the closed cells 235 of the third of the three layers of the third layer 214 may be facing or protruding downwards towards a second side of the tissue interface 114. In other embodiments, the three layers of the third layer 214 may be positioned so that the closed cells 235 are oriented in a variety of different combinations.

Figure 19:
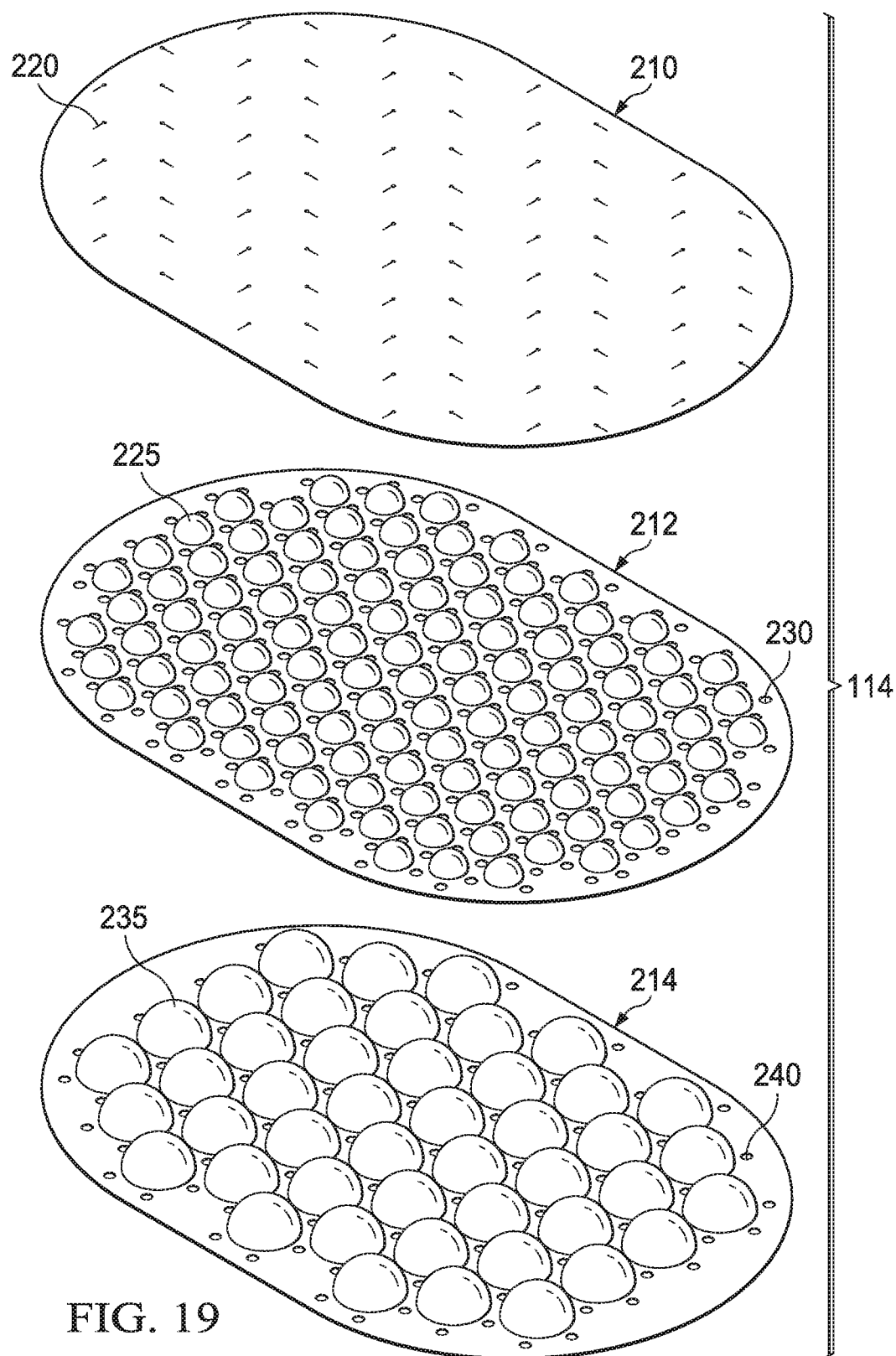
FIG. 19 is an assembly view of another example of a tissue interface, illustrating additional details that may be associated with some example embodiments of the therapy system of FIG. 1.

FIG. 19 is an assembly view of another example of the tissue interface 114 of FIG. 1. In the example of FIG. 19, the second layer 212 is disposed between the first layer 210 and the third layer 214. The embodiment of the tissue interface 114 illustrated in FIG. 19 may be such that the third layer 214 is adapted for being placed directly against a tissue site. For example, the tissue interface 114 of FIG. 19 may be a side-specific, as opposed to a reversible or side-independent structure. However, it may also be that the orientation of the tissue interface 114 of FIG. 19 may be reversed such that the first layer 210 is for positioning against a tissue site. Depending on which layer of the tissue interface 114 faces the tissue site, the tissue interface 114 of FIG. 19 may cause different responses from a tissue site. Additionally, the third layer 214 may be positioned so that the closed cells 235 either face upwards or downwards.

In the example of FIG. 19, the closed cells 235 of the third layer 214 may be positioned on an inward surface of the third layer 214, therefore, placing the closed cells 235 in contact with the second layer 212. The closed cells 235 may form a plurality of channels with the second layer 212 for providing passageways for fluid flow for both negative pressure and instillation liquids during therapy sessions. The apertures 240 of the third layer 214 may fluidly couple the channels formed between the third layer 214 and the second layer 212 with the voids to facilitate the transmission of negative pressure and the movement of fluids. As discussed above with respect to other example embodiments of the tissue interface 114, the apertures 240 placed between the closed cells 235 of the third layer of FIG. 19 may measure about 1 mm or greater in diameter.

If negative pressure is applied to the third layer 214, the third layer 214 may be compressed under the cover 116, which may cause the cover 116 to collapse toward the tissue site. For example, in embodiments where the orientation of the tissue interface 114 is such that the third layer 214 is adjacent to the cover 116, the collapsing force of the cover 116 downward on the upper surfaces of the closed cells 235 may be transmitted via the closed cells 235. In some embodiments, the third layer 214 may include nodes or projections. For example, the third layer 214 may be disposed at a tissue site so that the nodes extend outwardly from the third layer 214 and contact the tissue site. The nodes may form voids between the outside surface of the third layer 214 and the tissue site. The nodes may be compressed into the tissue site for increasing micro-strains on the tissue site for enhancing granulation. Although the closed cells 235 may change shape or flatten somewhat during the application of negative pressure to the third layer 214, the volume of the closed cells 235 can remain substantially constant. The third layer 214 can transmit downward forces to the nodes while maintaining fluid flow through the channels to continue providing negative-pressure therapy to the tissue site. Consequently, the third layer 214 can apply apposition forces to the nodes, which can enhance granulation while maintaining fluid communication with a tissue site via the channels and the voids. The flexibility of the closed cells 235 can also facilitate movement of the nodes as negative pressure increases and/or is varied during treatment so that the additional movement can further enhance granulation.

Figure 20:
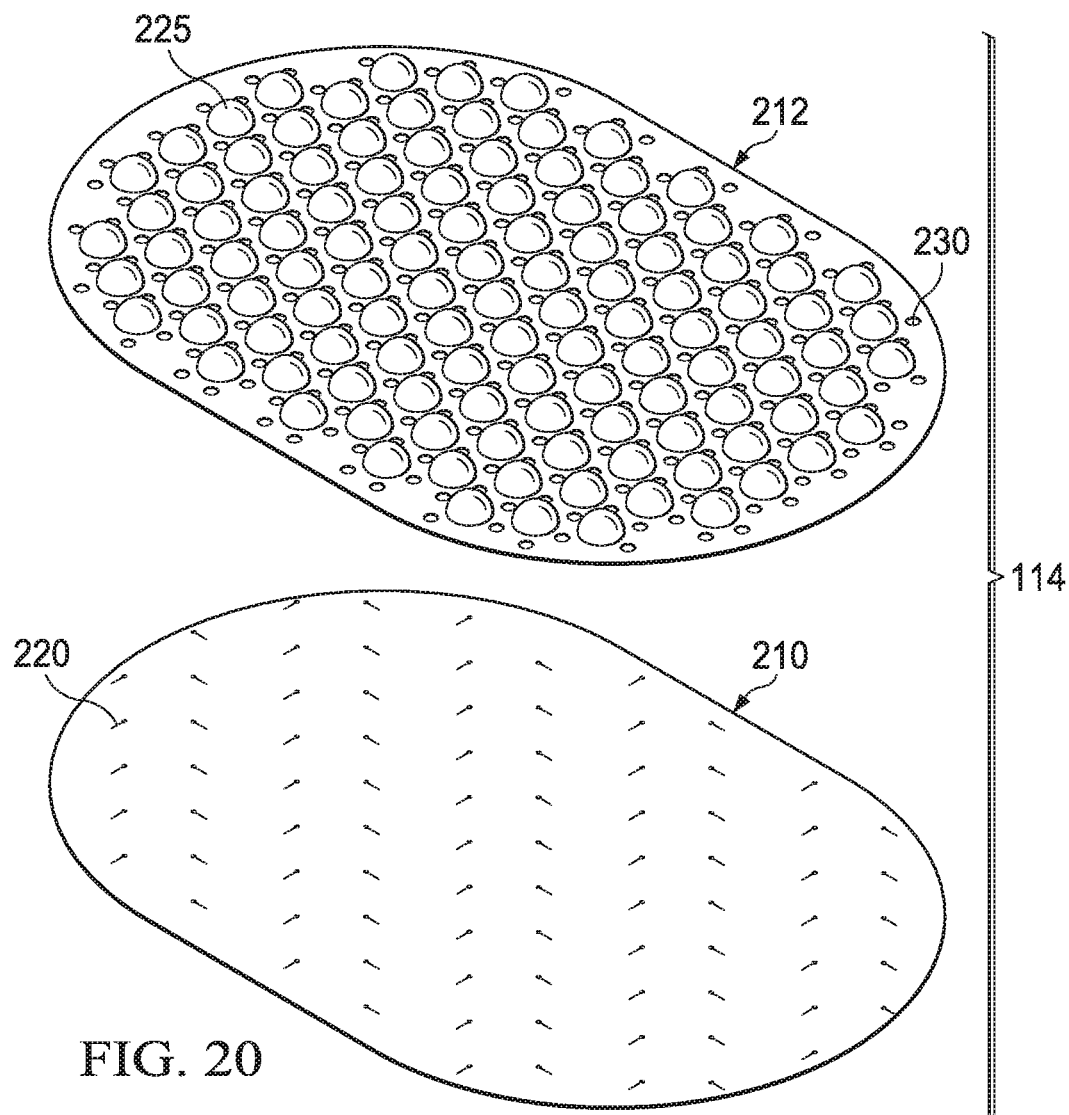
FIG. 20 is an assembly view of another example of a tissue interface, illustrating additional details that may be associated with some example embodiments of the therapy system of FIG. 1.

FIG. 20 is an assembly view of another example of the tissue interface 114 of FIG. 1. In the example of FIG. 20, the tissue interface 114 may include the first layer 210 and the second layer 212 disposed adjacent to the first layer 210. Thus, in some embodiments, the tissue interface 114 may be in the form of a two-layer construct for placing against a tissue site. Depending on the particular needs of the tissue site, the two-layer construct of the example tissue interface 114 of FIG. 20 may be placed with either the first layer 210 or the second layer 212 against the surface of the tissue site. Additionally, depending on the particular embodiment, the orientation of the second layer 212 may be reversed. For example, in some embodiments, the second layer 212 may be oriented against the first layer 210 so that the blisters 225 may protrude away from the first layer 210, as shown in the example of FIG. 20. In other embodiments, the second layer 212 may be oriented against the first layer 210 so that the blisters 225 face, or come into contact with the first layer 210.

Figure 21:
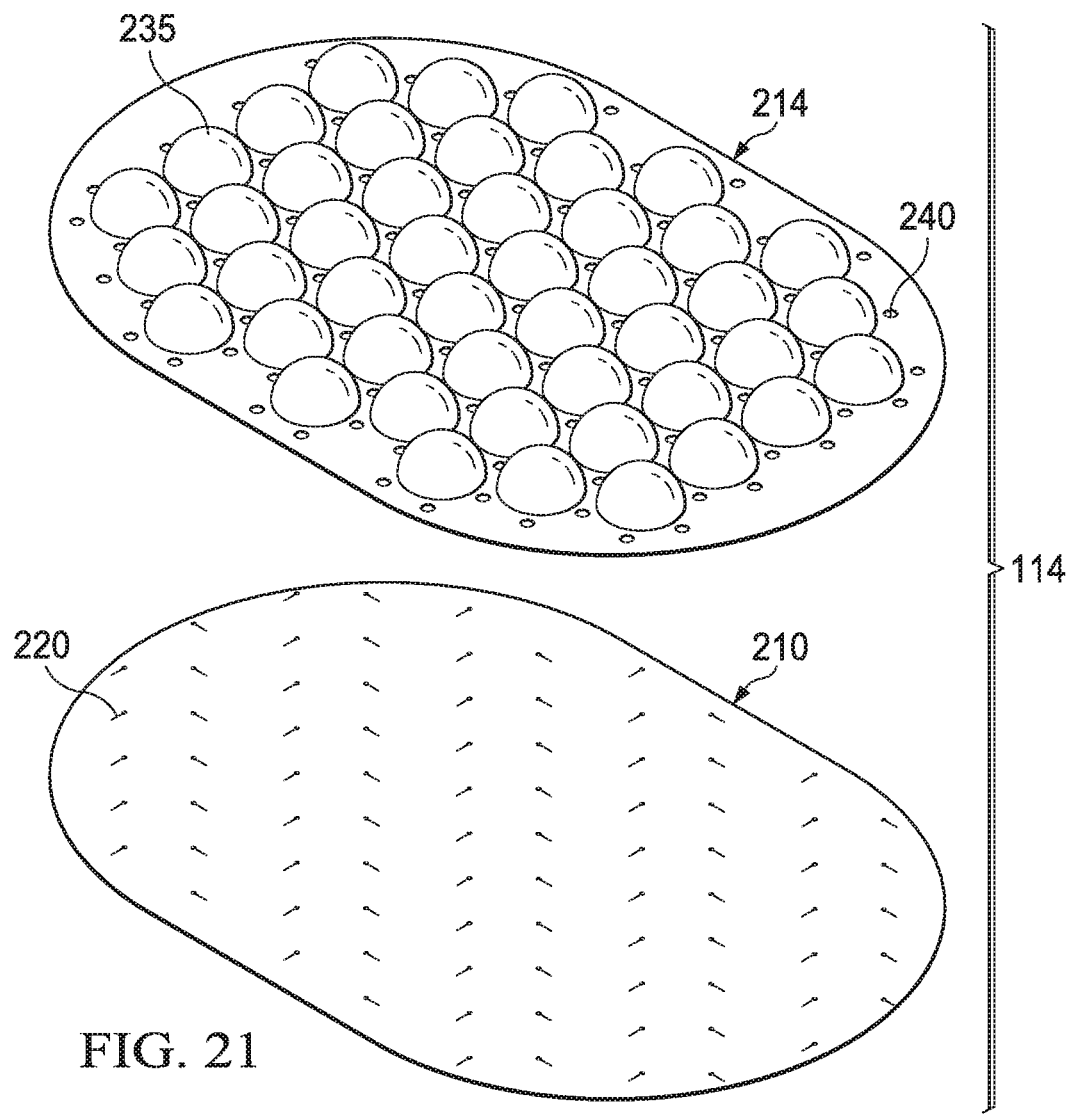
FIG. 21 is an assembly view of another example of a tissue interface, illustrating additional details that may be associated with some example embodiments of the therapy system of FIG. 1.

FIG. 21 is an assembly view of another example of the tissue interface 114 of FIG. 1. Similar to the example shown in FIG. 20, the tissue interface 114 of FIG. 21 may be in the form of a two-layer construct for placing against a tissue site. The tissue interface 114 of FIG. 21 may include the first layer 210 and the third layer 214 disposed adjacent to the first layer 210. The tissue interface 114 of FIG. 21 may be placed with either the first layer 210 or the third layer 214 against the surface of the tissue site. As mentioned with respect to FIG. 20, the orientation of the third layer 214 of the tissue interface 114 of FIG. 21 may be reversed so that the closed cells 235 either extend away from the first layer 210 (as shown in FIG. 21) or face the first layer 210.

In some additional embodiments, features of the first layer 210 and the third layer 214 of the tissue interface 114 may be combined to a certain extent. For example, the third layer 214, which ordinarily may be formed from two sheets of polymeric film, may include the first layer 210 as one of the two sheets of polymeric film. In such instances, the closed cells 235 of the third layer 214 may be formed between, or encapsulated by, the first layer 210 on a first side and a second sheet of polymeric film on a second side. The fluid restrictions 220 of the first layer 210 may be positioned between or around the closed cells 235.

Additional or alternative embodiments of the dressing 104 and, in particular, tissue interface 114 may be provided depending on the particular application or tissue site presented. For example, in some embodiments, one or more of the layers of the tissue interface 114, such as the first layer 210, second layer 212, and third layer 214, may comprise an alternative material(s) such as, for example, a closed-cell foam such as a ZOTEFOAM material. A closed-cell foam material may be self-supporting, yet also flexible, and may also permit open air pockets to be formed in the material, rather than only closed-cell versions. Including multiple layers of such a foam material may offer some benefits in simplifying the construction of the tissue interface 114.

In some other example embodiments of the tissue interface 114, the third layer 214 may be provided with closed cells that may be formed by printing a component across the surface of the third layer 214 that may later expand and provide trapped air pockets. For example, a polymer solution, suspension, or emulsion that contains a blowing agent may be printed across a surface of the third layer 214. Once the printed component on the third layer 214 is dry, heat may be applied to activate the blowing agent, expanding the printed component. This method of forming the closed cells may help simplify the lamination process of the various layers of the tissue interface 114, by allowing multiple flat film layers to be laminated and then the layers bonded together while also expanded, in one heating process.

Depending on the particular embodiment of the tissue interface 114, different mechanisms for bonding together the various film layers of the tissue interface 114 may be used. For example, the film layers of the tissue interface 114 may be formed from film laminates, for example polyethylene/ionomer laminates, where the ionomer is a low-melting point polymer that will soften under low heat, thus, enabling the different film layers of the tissue interface 114 to be bonded together. Therefore, in some instances, the need for a separately-applied hot melt mesh may be eliminated. Additionally or alternatively, the bonding surfaces of the various film layers of the tissue interface 114 may be sprayed with a pressure-sensitive or heat-reactive adhesive just prior to lamination of the film layers. Furthermore, in embodiments where a low-melting point hot-melt mesh is used to bond the various layers of the tissue interface 114 together, the hot-melt mesh may be made heat crosslinkable to provide additional heat stability. Additionally, all of the various adhesives described above may be made susceptible to crosslinking, for example by gamma irradiation, in order to increase bond strength and improve heat stability.

The systems, apparatuses, and methods described herein may provide significant advantages. For example, some embodiments of the dressing 104 may provide a tissue dressing for use with negative-pressure therapy that is simple to apply, and can reduce the amount of time needed to apply and remove the dressing. Waste associated with improper application of dressing materials can also be reduced. In some embodiments, the tissue interface 114, and in some instances the dressing 104, may be a fully-integrated negative-pressure therapy dressing that can be readily cut, shaped, and customized by an operator for application to a tissue site. Unlike some instances of prior dressings, the tissue interface 114 or dressing 104 may be cut and shaped without exposing foam or other materials which may allow in-growth of tissue and, thus, lead to disruption of the tissue site during dressing removal. The dressing 104 can provide good interaction with tissue at a tissue site, including good manifolding of negative pressure and therapeutic fluids provided in conjunction with instillation therapy. For example, the inclusion of manifolding or spacing layers, such as the second layer 212 and the third layer 214, within the tissue interface 114 may provide good manifolding with a compressible, soft material filler that can conform to spaces and curves. Thus, the dressing 104 may offer beneficial granulation and a low-trauma and high-seal bond with the tissue site, without necessarily becoming incorporated with the tissue site as may occur with prior dressings in the art.

Inclusion of different layers in the tissue interface 114 can provide a structure for filling deeper tissue sites, such as medium-to-deep wounds, while substantially reducing or preventing disruptive in-growth into the tissue interface 114 and dressing 104. These characteristics of the dressing 104 may be particularly advantageous for placing within deep wounds or cavities of undermined regions, while maintaining the ability of easy removal. In some instances, the dressing 104 may provide a wound filler which may safely remain in place at the tissue site for up to 7 days, or even longer. Furthermore, multiple layers of the dressing 104 may be formed from transparent materials, which may enable a user to maintain a view of the tissue site for observing any color or other aspects of the tissue site related to infection or other conditions.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for use with negative-pressure treatment, the dressing comprising:
   a first layer comprising a first film of non-porous material and plurality of fluid restrictions;
   a second layer adjacent to the first layer, the second layer comprising a second film of non-porous material having blisters and first apertures to allow fluid transfer through the second film;
   a third layer comprising a non-porous material having closed cells and second apertures between the closed cells to allow fluid transfer through the third layer;

a fourth layer adjacent to the third layer opposite the second layer, the fourth layer comprising a third film of non-porous material having blisters and third apertures to allow fluid transfer through the fourth layer; and a fifth layer adjacent to the fourth layer opposite the third layer, the fifth layer comprising a fourth film of non-porous material and a second plurality of fluid restrictions.

2. The dressing of claim 1, further comprising fluid contained in the closed cells.

3. The dressing of claim 1, wherein the first film is a hydrophobic polymer film.

4. The dressing of claim 1, wherein the first film is a polyethylene film.

5. The dressing of claim 1, wherein the fluid restrictions comprise or consist essentially of elastomeric valves that are normally closed and open in response to a pressure gradient across the first film.

6. The dressing of claim 1, wherein the fluid restrictions comprise linear fenestrations, each of the linear fenestrations having a length not greater than 4 millimeters.

7. The dressing of claim 1, wherein the fluid restrictions comprise a plurality of linear perforations, each of the linear perforations having a length not greater than 4 millimeters and a width not greater than 2 millimeters.

8. The dressing of claim 1, wherein the fluid restrictions are coextensive with the first film.

9. The dressing of claim 1, wherein the fluid restrictions are distributed across the first film in a uniform pattern.

10. The dressing of claim 1, wherein the fluid restrictions are distributed across the first film in a grid of parallel rows and columns.

11. The dressing of claim 1, wherein the blisters are spaced about 2 millimeters apart.

12. The dressing of claim 1, wherein the blisters have a height of about 1.5 millimeters.

13. The dressing of claim 1, wherein the blisters have a width of about 1.5 millimeters.

14. The dressing of claim 1, wherein:
the blisters are spaced about 2 millimeters apart;
the blisters have a height of about 1.5 millimeters; and
the blisters have a diameter of about 1.5 millimeters.

15. The dressing of claim 1, wherein the second film is polyurethane.

16. The dressing of claim 1, wherein:
the non-porous material of the third layer comprises two films bonded together; and
the closed cells are defined by the two films.

17. The dressing of claim 1, wherein:
the non-porous material of the third layer comprises two films bonded together;
the closed cells are defined by the two films; and
both of the two films comprise polyolefin.

* * * * *